US011534581B2

(12) United States Patent
Isaacson et al.

(10) Patent No.: US 11,534,581 B2
(45) Date of Patent: Dec. 27, 2022

(54) PORTED IV CATHETER HAVING EXTERNAL NEEDLE SHIELD AND INTERNAL BLOOD CONTROL SEPTUM

(71) Applicant: Becton, Dickinson and Company, Franklin Lakes, NJ (US)

(72) Inventors: S. Ray Isaacson, Layton, UT (US); Stephen T. Bornhoft, Midvale, UT (US); Weston F. Harding, Lehi, UT (US); Yiping Ma, Layton, UT (US); Siddarth K. Shevgoor, Mission Viejo, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 308 days.

(21) Appl. No.: 16/678,650

(22) Filed: Nov. 8, 2019

(65) Prior Publication Data

US 2020/0094026 A1      Mar. 26, 2020

Related U.S. Application Data

(63) Continuation of application No. 14/295,953, filed on Jun. 4, 2014, now Pat. No. 10,500,376.
(Continued)

(51) Int. Cl.
*A61M 25/06* (2006.01)
*A61M 25/00* (2006.01)
(Continued)

(52) U.S. Cl.
CPC .... *A61M 25/0625* (2013.01); *A61M 25/0009* (2013.01); *A61M 25/0014* (2013.01);
(Continued)

(58) Field of Classification Search
CPC .............. A61M 25/06; A61M 25/0606; A61M 25/0612; A61M 25/0618; A61M 25/0625;
(Continued)

(56) References Cited

U.S. PATENT DOCUMENTS

| | | | |
|---|---|---|---|
| 3,585,996 | A | 6/1971 | Reynolds et al. |
| 4,332,249 | A | 6/1982 | Joslin |

(Continued)

FOREIGN PATENT DOCUMENTS

| | | |
|---|---|---|
| AU | 2006203664 A1 | 2/2008 |
| CA | 2133053 A1 | 3/1995 |

(Continued)

OTHER PUBLICATIONS

Singapore Office Action dated Jan. 29, 2020 in Singapore Patent Application No. 11201708370P.
(Continued)

*Primary Examiner* — James D Ponton
(74) *Attorney, Agent, or Firm* — Dickinson Wright PLLC

(57) ABSTRACT

An extravascular system is provided which includes a catheter adapter having a blood control septum configured to control flow of a fluid through the catheter adapter, the catheter adapter further having a catheter configured for intravenous insertion. The extravascular system further includes a septum activator slidably inserted within the catheter adapter and configured for advancement through the blood control septum to provide a fluid pathway through the blood control septum. Further still, the extravascular system includes an external safety mechanism comprising a needle hub and a needle shield interconnected via a tether, wherein the needle shield includes a safety clip that is configured to retain a sharpened end of the introducer needle within the needle shield. Some implementations further comprise an access port forming a portion of the catheter adapter and
(Continued)

providing selective access to the lumen of the catheter adapter.

16 Claims, 43 Drawing Sheets

Related U.S. Application Data

(60) Provisional application No. 61/832,512, filed on Jun. 7, 2013.

(51) Int. Cl.
    *A61M 39/06* (2006.01)
    *A61M 39/00* (2006.01)
    *A61M 5/158* (2006.01)
    *A61M 5/32* (2006.01)
    *A61M 5/162* (2006.01)

(52) U.S. Cl.
    CPC .... *A61M 25/0015* (2013.01); *A61M 25/0097* (2013.01); *A61M 25/0606* (2013.01); *A61M 25/0618* (2013.01); *A61M 39/00* (2013.01); *A61M 39/0606* (2013.01); *A61M 5/158* (2013.01); *A61M 5/1626* (2013.01); *A61M 5/3275* (2013.01); *A61M 25/0693* (2013.01); *Y10T 29/49826* (2015.01)

(58) Field of Classification Search
    CPC .......... A61M 25/0631; A61M 25/0009; A61M 25/0014; A61M 25/0015; A61M 25/0097; A61M 5/3275; A61M 5/3243; A61M 5/158; A61M 39/0693; A61M 39/00; A61M 39/0606; A61M 2005/3247
    See application file for complete search history.

(56) References Cited

U.S. PATENT DOCUMENTS

| | | |
|---|---|---|
| 4,387,879 A | 6/1983 | Tauschinski |
| 4,424,817 A | 1/1984 | Williams |
| 4,524,805 A | 6/1985 | Hoffman |
| 4,622,964 A | 11/1986 | Flynn |
| 4,762,516 A | 8/1988 | Luther et al. |
| 4,809,679 A | 3/1989 | Shimonaka et al. |
| 4,842,591 A | 6/1989 | Luther |
| 4,850,961 A | 7/1989 | Wanderer et al. |
| 4,871,356 A * | 10/1989 | Haindl .................. A61M 25/00 604/247 |
| 4,917,668 A | 4/1990 | Haindl |
| 4,946,133 A | 8/1990 | Johnson et al. |
| 4,948,092 A | 8/1990 | Kasper et al. |
| 4,978,344 A | 12/1990 | Dombrowski et al. |
| 5,000,740 A | 3/1991 | Ducharme et al. |
| 5,032,116 A | 7/1991 | Peterson et al. |
| 5,053,014 A | 10/1991 | Van Heugten |
| 5,084,023 A * | 1/1992 | Lemieux ........... A61M 39/0606 604/167.02 |
| 5,092,845 A | 3/1992 | Chang |
| 5,098,405 A | 3/1992 | Peterson |
| 5,108,380 A | 4/1992 | Herlitze et al. |
| 5,156,596 A | 10/1992 | Balbierz |
| 5,215,528 A | 6/1993 | Purdy et al. |
| 5,228,453 A | 7/1993 | Sepetka |
| 5,290,246 A | 3/1994 | Yamamoto et al. |
| 5,300,045 A | 4/1994 | Plassche, Jr. |
| 5,322,518 A | 6/1994 | Schneider et al. |
| 5,328,482 A | 7/1994 | Sircom et al. |
| 5,348,544 A | 9/1994 | Sweeney et al. |
| 5,391,152 A | 2/1995 | Patterson |
| 5,405,323 A | 4/1995 | Rogers et al. |
| 5,419,766 A | 5/1995 | Chang et al. |
| 5,423,766 A | 6/1995 | Di Cesare |
| 5,458,658 A | 10/1995 | Sircom |
| 5,501,675 A | 3/1996 | Erskine |
| 5,538,508 A | 7/1996 | Steyn |
| 5,558,651 A | 9/1996 | Crawford et al. |
| 5,575,777 A | 11/1996 | Cover et al. |
| 5,584,809 A | 12/1996 | Gaba |
| 5,596,996 A | 1/1997 | Johanson |
| 5,662,610 A | 9/1997 | Sircom |
| 5,697,907 A | 12/1997 | Gaba |
| 5,718,688 A | 2/1998 | Wozencroft |
| 5,749,857 A | 5/1998 | Cuppy |
| 5,772,636 A | 6/1998 | Brimhall et al. |
| 5,817,069 A | 10/1998 | Arnett |
| 5,851,196 A | 12/1998 | Arnett |
| 5,858,002 A | 1/1999 | Jesch |
| 5,911,710 A | 6/1999 | Berry et al. |
| 5,954,698 A | 9/1999 | Pike |
| 5,967,490 A | 10/1999 | Pike |
| 6,001,080 A | 12/1999 | Kuracina et al. |
| 6,042,876 A | 3/2000 | Deem |
| 6,117,108 A | 9/2000 | Woehr et al. |
| 6,213,978 B1 | 4/2001 | Voyten |
| 6,221,047 B1 | 4/2001 | Greene et al. |
| 6,224,569 B1 | 5/2001 | Brimhall et al. |
| 6,379,333 B1 | 4/2002 | Brimhall et al. |
| 6,425,884 B1 | 7/2002 | Wemmert et al. |
| 6,506,181 B2 | 1/2003 | Meng et al. |
| 6,595,981 B2 | 7/2003 | Huet |
| 6,616,630 B1 | 9/2003 | Woehr et al. |
| 6,652,486 B2 | 11/2003 | Bialecki et al. |
| 6,709,419 B2 | 3/2004 | Woehr |
| 6,749,588 B1 | 6/2004 | Howell et al. |
| 6,972,002 B2 | 12/2005 | Thone |
| RE38,996 E | 2/2006 | Crawford et al. |
| 7,008,404 B2 | 3/2006 | Nakajima |
| 7,029,492 B1 | 4/2006 | Mitsudou et al. |
| 7,226,434 B2 | 6/2007 | Carlyon et al. |
| 7,267,661 B2 | 9/2007 | Susi |
| 7,500,965 B2 | 3/2009 | Menzi et al. |
| 7,597,681 B2 | 10/2009 | Sutton et al. |
| 7,632,245 B1 | 12/2009 | Cowan et al. |
| 7,651,476 B2 | 1/2010 | Kohler |
| 7,682,340 B2 | 3/2010 | Funamura et al. |
| 7,722,569 B2 | 5/2010 | Soderholm et al. |
| 7,736,332 B2 | 6/2010 | Carlyon et al. |
| 7,736,339 B2 | 6/2010 | Woehr et al. |
| 7,744,567 B2 | 6/2010 | Glowacki et al. |
| 7,935,080 B2 | 5/2011 | Howell |
| 7,988,664 B2 | 8/2011 | Fiser et al. |
| 8,062,261 B2 | 11/2011 | Adams |
| 8,308,691 B2 | 11/2012 | Woehr et al. |
| 8,328,762 B2 | 12/2012 | Woehr et al. |
| 8,333,735 B2 | 12/2012 | Woehr et al. |
| 8,337,463 B2 | 12/2012 | Woehr et al. |
| 8,348,893 B2 | 1/2013 | Carlyon |
| 8,357,119 B2 | 1/2013 | Stout et al. |
| 8,361,020 B2 | 1/2013 | Stout |
| 8,361,038 B2 | 1/2013 | McKinnon et al. |
| 8,382,718 B2 | 2/2013 | Woehr |
| 8,388,583 B2 | 3/2013 | Stout et al. |
| 8,414,539 B1 | 4/2013 | Kuracina et al. |
| 8,419,688 B2 | 4/2013 | Woehr et al. |
| 8,444,605 B2 | 5/2013 | Kuracina et al. |
| 8,460,247 B2 | 6/2013 | Woehr et al. |
| 8,469,928 B2 | 6/2013 | Stout et al. |
| 8,496,623 B2 | 7/2013 | Burkholz |
| 8,523,828 B2 | 9/2013 | Callahan |
| 8,540,728 B2 | 9/2013 | Woehr et al. |
| 8,545,454 B2 | 10/2013 | Kuracina et al. |
| 8,591,467 B2 | 11/2013 | Walker et al. |
| 8,591,468 B2 | 11/2013 | Woehr et al. |
| 8,597,249 B2 | 12/2013 | Woehr et al. |
| 8,679,063 B2 | 3/2014 | Stout et al. |
| 8,740,859 B2 | 6/2014 | McKinnon et al. |
| 8,764,711 B2 | 7/2014 | Kuracina et al. |
| 8,926,564 B2 | 1/2015 | King et al. |
| 8,939,938 B2 | 1/2015 | Funamura et al. |
| 8,951,230 B2 | 2/2015 | Tanabe et al. |
| 9,056,188 B2 | 6/2015 | Hager et al. |

(56) References Cited

U.S. PATENT DOCUMENTS

| | | |
|---|---|---|
| 9,089,671 B2 | 7/2015 | Stout et al. |
| 9,114,241 B2 | 8/2015 | Stout et al. |
| 9,149,625 B2 | 10/2015 | Woehr et al. |
| 9,149,626 B2 | 10/2015 | Woehr et al. |
| 8,932,259 B2 | 11/2015 | Stout et al. |
| 9,358,364 B2 | 6/2016 | Isaacson et al. |
| 9,370,641 B2 | 6/2016 | Woehr et al. |
| 9,408,632 B2 | 8/2016 | Erskine |
| 9,592,152 B2 | 3/2017 | Griffis et al. |
| 9,717,886 B2 | 8/2017 | Kuehn et al. |
| 10,729,890 B2 | 8/2020 | Harding et al. |
| 2001/0053895 A1 | 12/2001 | Vaillancourt |
| 2002/0128604 A1 | 9/2002 | Nakajima |
| 2002/0169418 A1 | 11/2002 | Menzi et al. |
| 2003/0057392 A1 | 3/2003 | Ito |
| 2003/0060774 A1 | 3/2003 | Woehr et al. |
| 2003/0195471 A1 | 10/2003 | Woehr et al. |
| 2004/0116856 A1 | 6/2004 | Woehr et al. |
| 2004/0204689 A1 | 10/2004 | Lynn |
| 2004/0225260 A1 | 11/2004 | Villa et al. |
| 2005/0010176 A1 | 1/2005 | Dikeman et al. |
| 2005/0043684 A1 | 2/2005 | Basta et al. |
| 2005/0075609 A1 | 4/2005 | Latona |
| 2005/0107740 A1 | 5/2005 | Jensen et al. |
| 2005/0113755 A1 | 5/2005 | Greene et al. |
| 2006/0074384 A1 | 4/2006 | Kohler |
| 2006/0155245 A1 | 7/2006 | Woehr |
| 2006/0178635 A1 | 8/2006 | Callaway |
| 2006/0200080 A1 | 9/2006 | Abulhaj |
| 2006/0264828 A1 | 11/2006 | Woehr et al. |
| 2007/0038186 A1 | 2/2007 | Sutton et al. |
| 2007/0083162 A1 | 4/2007 | O'Reagan et al. |
| 2007/0129689 A1 | 6/2007 | Woehr et al. |
| 2007/0176414 A1 | 8/2007 | McBee et al. |
| 2007/0233007 A1 | 10/2007 | Adams |
| 2007/0270754 A1* | 11/2007 | Soderholm ........ A61M 25/0637 604/164.08 |
| 2008/0065015 A1 | 3/2008 | Fisher et al. |
| 2008/0097343 A1 | 4/2008 | Woehr |
| 2008/0140004 A1 | 6/2008 | Thorne |
| 2008/0140011 A1 | 6/2008 | Hager et al. |
| 2008/0147009 A1 | 6/2008 | Nilsson |
| 2008/0208132 A1 | 8/2008 | Funamura et al. |
| 2008/0243086 A1 | 10/2008 | Hager et al. |
| 2009/0157013 A1 | 6/2009 | Wong |
| 2009/0163861 A1 | 6/2009 | Carlyon |
| 2009/0182280 A1 | 7/2009 | Glowacki et al. |
| 2009/0281499 A1 | 11/2009 | Harding et al. |
| 2009/0312711 A1 | 12/2009 | Brimhall |
| 2010/0137803 A1 | 6/2010 | Funamura et al. |
| 2010/0191189 A1 | 7/2010 | Harding et al. |
| 2010/0204648 A1 | 8/2010 | Stout et al. |
| 2010/0204660 A1 | 8/2010 | McKinnon et al. |
| 2010/0217208 A1 | 8/2010 | Snow |
| 2010/0222746 A1 | 9/2010 | Burkholz |
| 2011/0046570 A1 | 2/2011 | Stout et al. |
| 2011/0054403 A1 | 3/2011 | Tanabe et al. |
| 2011/0160662 A1 | 6/2011 | Stout et al. |
| 2011/0213307 A1 | 9/2011 | Kawai et al. |
| 2011/0288482 A1 | 11/2011 | Farrell et al. |
| 2012/0065612 A1* | 3/2012 | Stout .................... A61M 39/06 604/500 |
| 2012/0078200 A1 | 3/2012 | Woehr et al. |
| 2012/0123354 A1 | 5/2012 | Woehr |
| 2012/0136311 A1 | 5/2012 | Knutsson |
| 2012/0220957 A1 | 8/2012 | Kuracina et al. |
| 2012/0238966 A1 | 9/2012 | Kuracina et al. |
| 2012/0277679 A1 | 11/2012 | Steube |
| 2013/0030370 A1 | 1/2013 | Walker et al. |
| 2013/0090607 A1 | 4/2013 | McKinnon |
| 2013/0090609 A1 | 4/2013 | Sonderegger et al. |
| 2013/0178807 A1 | 7/2013 | Baid |
| 2013/0184645 A1 | 7/2013 | Baid |
| 2013/0226141 A1 | 8/2013 | King et al. |
| 2013/0245587 A1 | 9/2013 | Tremblay |
| 2013/0253443 A1 | 9/2013 | Woehr et al. |
| 2013/0324930 A1 | 12/2013 | Fuchs et al. |
| 2014/0012203 A1 | 1/2014 | Woehr et al. |
| 2014/0018738 A1 | 1/2014 | Steube |
| 2014/0276434 A1 | 9/2014 | Woehr et al. |
| 2014/0364809 A1 | 12/2014 | Isaacson et al. |
| 2015/0151088 A1 | 6/2015 | Lim et al. |
| 2016/0015941 A1 | 1/2016 | Tanabe et al. |
| 2016/0106959 A1 | 4/2016 | Woehr |
| 2016/0114137 A1 | 4/2016 | Woehr et al. |
| 2016/0158503 A1 | 6/2016 | Woehr |
| 2016/0158526 A1 | 6/2016 | Woehr |
| 2017/0348518 A1 | 12/2017 | Ma et al. |

FOREIGN PATENT DOCUMENTS

| | | |
|---|---|---|
| CN | 1758929 A | 4/2006 |
| CN | 1871043 A | 11/2006 |
| CN | 101791447 A | 8/2010 |
| CN | 202005932 U | 10/2011 |
| CN | 202682467 U | 1/2013 |
| CN | 106470607 A | 3/2017 |
| EP | 0352928 A1 | 1/1990 |
| EP | 1558311 A1 | 8/2008 |
| EP | 2204204 A1 | 7/2010 |
| EP | 2228093 A1 | 9/2010 |
| EP | 2319556 A1 | 5/2011 |
| EP | 2343095 A1 | 7/2011 |
| EP | 2489393 A1 | 8/2012 |
| EP | 2566543 A1 | 3/2013 |
| EP | 2617447 A2 | 7/2013 |
| EP | 1656168 B1 | 12/2013 |
| EP | 2803376 A1 | 11/2014 |
| GB | 2508570 B | 6/2014 |
| JP | H1057497 A | 3/1998 |
| JP | 2001-514943 A | 9/2001 |
| JP | 2002126080 A | 5/2002 |
| JP | 2002-263197 A | 9/2002 |
| JP | 3786312 B2 | 3/2006 |
| JP | 2008-173206 A | 7/2008 |
| JP | 2009538187 | 11/2009 |
| JP | 2010510038 A | 4/2010 |
| JP | 2010510039 | 4/2010 |
| JP | 4518609 B2 | 5/2010 |
| JP | 2010099534 A | 5/2010 |
| JP | 2014528330 | 10/2010 |
| JP | 2011-115630 A | 6/2011 |
| JP | 3170612 | 9/2011 |
| JP | 2012-517326 A | 8/2012 |
| JP | 2013115630 A | 6/2013 |
| JP | 2013-192868 A | 9/2013 |
| JP | 2014528331 | 10/2014 |
| JP | 2015-160061 A | 9/2015 |
| JP | 2015-173972 A | 10/2015 |
| JP | 2017533770 A | 11/2017 |
| SG | 173383 A1 | 8/2011 |
| WO | WO-1993005840 A2 | 4/1993 |
| WO | WO-1995022364 A1 | 8/1995 |
| WO | 9924092 | 5/1999 |
| WO | WO-2001012249 A1 | 2/2001 |
| WO | 0193940 A2 | 12/2001 |
| WO | 0195958 A1 | 12/2001 |
| WO | WO-2001093940 A2 | 12/2001 |
| WO | WO-2003011381 A1 | 2/2003 |
| WO | WO-2004004819 A1 | 1/2004 |
| WO | WO-2005042073 A1 | 5/2005 |
| WO | WO-2007139740 | 12/2007 |
| WO | 2008064332 A2 | 5/2008 |
| WO | WO-2008052791 A1 | 5/2008 |
| WO | WO-2008064332 A2 | 5/2008 |
| WO | 2009154824 A1 | 12/2009 |
| WO | WO-2010093791 A1 | 8/2010 |
| WO | WO-2012009028 A1 | 1/2012 |
| WO | WO-2012020633 A1 | 2/2012 |
| WO | WO-2012133428 A1 | 10/2012 |
| WO | WO-2013014639 A1 | 1/2013 |
| WO | 2013052666 A1 | 4/2013 |
| WO | WO-2013051242 A1 | 4/2013 |
| WO | WO-2013052661 A1 | 4/2013 |

(56) References Cited

FOREIGN PATENT DOCUMENTS

| WO | WO-2013052665 A2 | 4/2013 |
| WO | 2013137348 A1 | 9/2013 |
| WO | 2013162461 A1 | 10/2013 |
| WO | WO-2014054166 A1 | 4/2014 |
| WO | 2014126865 A1 | 8/2014 |
| WO | 2014197656 A1 | 12/2014 |
| WO | WO-2015024904 A1 | 2/2015 |
| WO | 2015161296 A1 | 10/2015 |
| WO | 2016077234 A1 | 5/2016 |
| WO | 2014162377 A1 | 2/2017 |

OTHER PUBLICATIONS

Japanese Office Action dated Jan. 28, 2020 in Japanese Patent Application No. 2017-554341.
US 5,755,409, 08/1979, Sigmund (withdrawn)
Dual Protection Safety I.V. Catheter Supercath (TM) 5, a New Generation of Safety I.V. Catheter, www.medikit.co.jp/english/.
Singapore Office Action dated Nov. 12, 2019 in Singapore Patent Application No. 11201708371S.
Brazilian Office Action dated Feb. 4, 2020 in Brazilian Patent Application No. 112015030658-6.

* cited by examiner

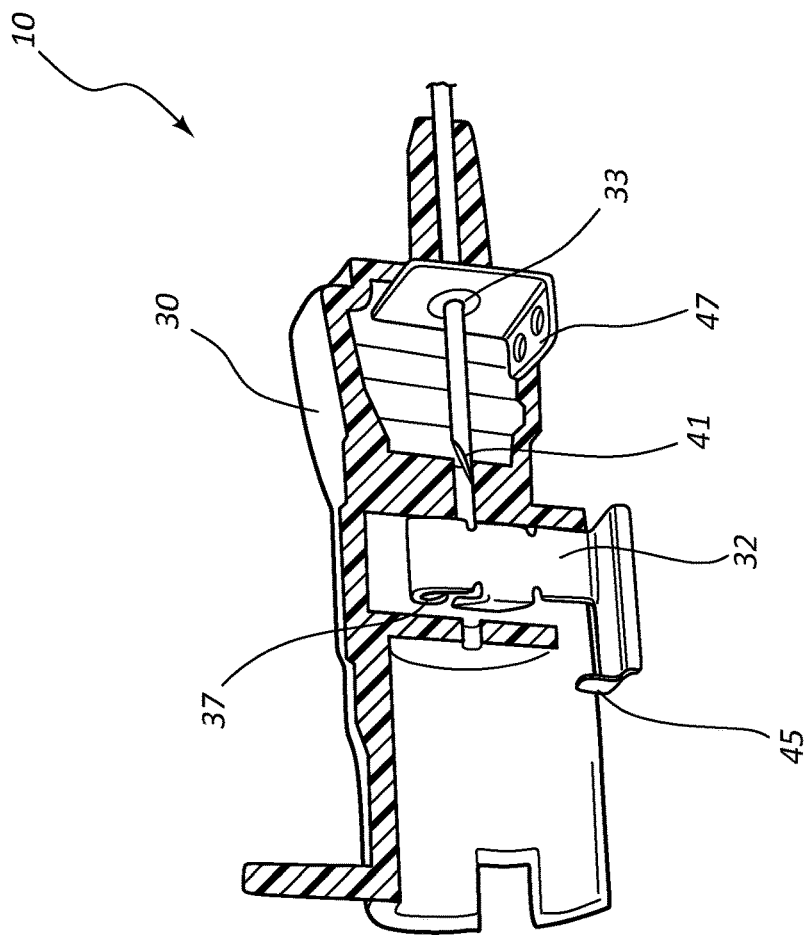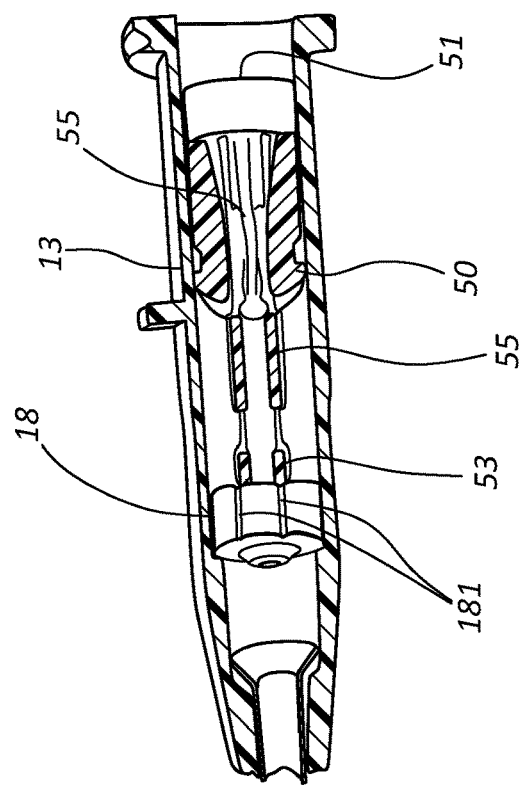
FIG. 7E

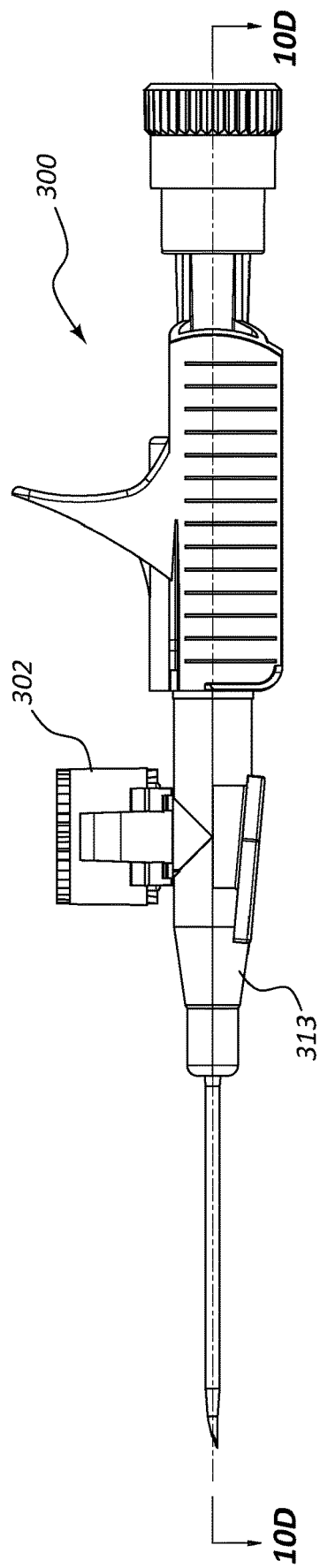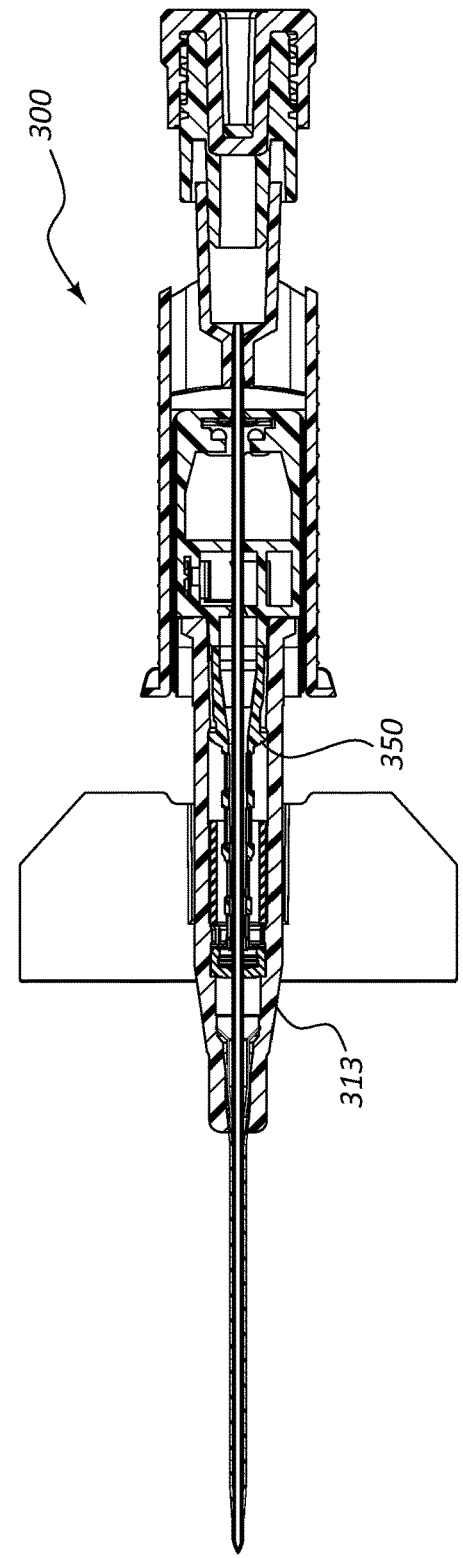
FIG. 10C
FIG. 10D

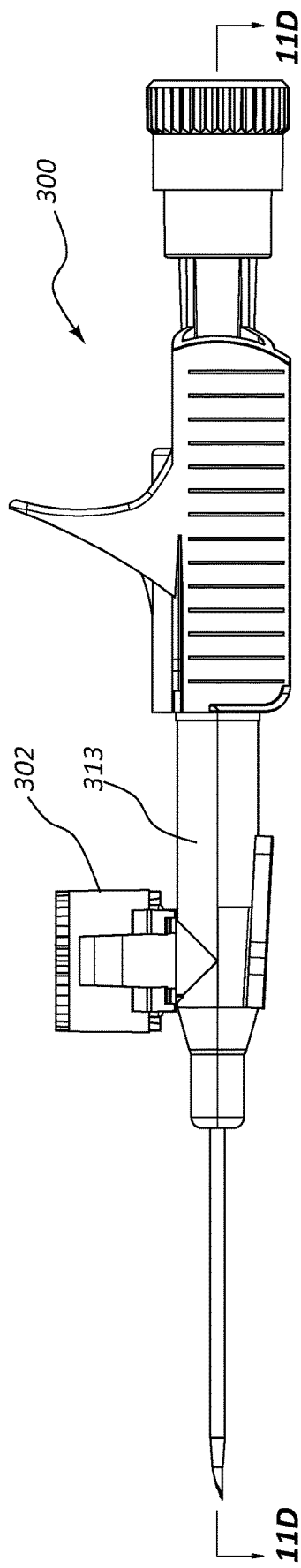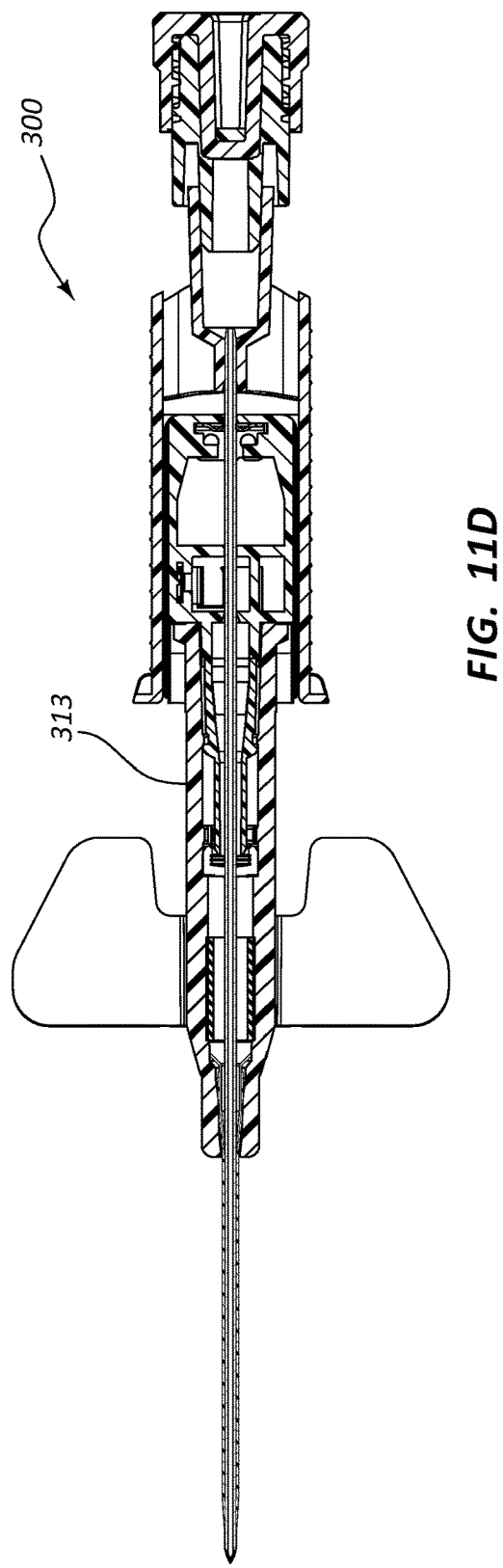
FIG. 11C
FIG. 11D

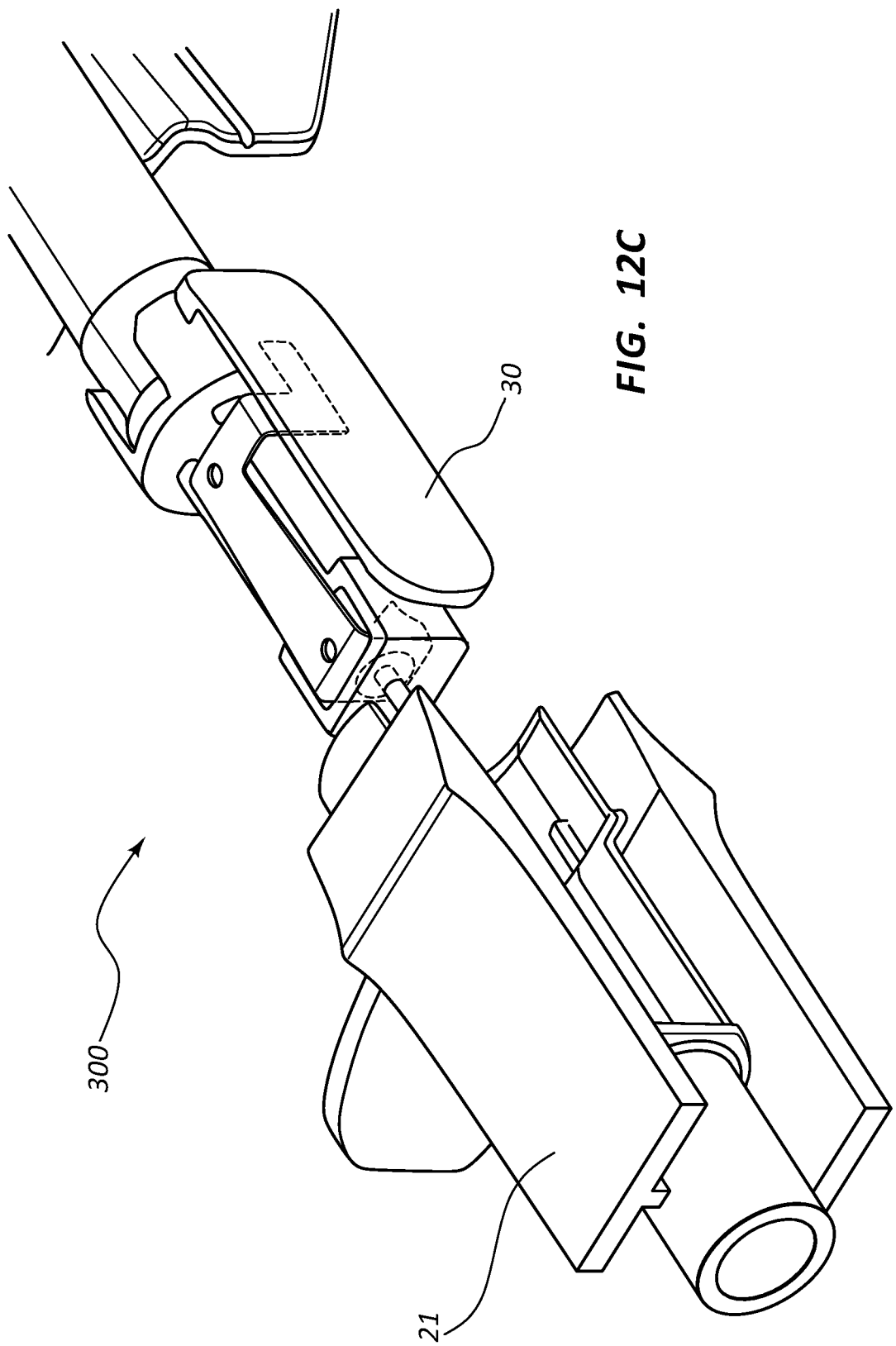

PORTED IV CATHETER HAVING EXTERNAL NEEDLE SHIELD AND INTERNAL BLOOD CONTROL SEPTUM

RELATED APPLICATIONS

This application is a continuation of U.S. patent application Ser. No. 14/295,953 filed on Jun. 4, 2014, which claims the benefit under 35 U.S.C. § 119(e) of U.S. Provisional Application No. 61/832,512, filed Jun. 7, 2013. The disclosures of all of these applications are incorporated herein by reference in their entirety.

FIELD OF THE INVENTION

The present invention relates to various intravenous (IV) catheter devices having an integrated external needle safety mechanism, an internal blood control valve or septum, and integrated septum activator. More particularly, the present invention relates to an IV catheter assembly having a catheter adapter comprising a blood control septum, and a needle shield selectively coupled to a proximal end of the catheter adapter. The needle shield is configured to catch and retain the sharpened, distal point of an introducer needle following catheterization of a patient. The septum activator is advanced through the blood control septum to provide a fluid pathway therethrough. In some instances the septum activator is advanced through the blood control septum by inserting a Luer device into the catheter adapter as part of an infusion procedure. Some implementations of the present invention further comprise a needle shield that is tethered to a needle hub such that the needle hub, introducer needle, and needle shield form a unitary structure that is removed from the catheter adapter following a catheterization procedure.

BACKGROUND OF THE INVENTION

Generally, vascular access devices are used for communicating fluid with the vascular system of patients. For example, catheters are used for infusing fluid, such as normal saline solution, various medicaments, and total parenteral nutrition, into a patient, withdrawing blood from a patient, or monitoring various parameters of the patient's vascular system.

A common type of intravenous (IV) catheter is an over-the-needle peripheral IV catheter. As its name implies, an over-the-needle catheter is mounted over an introducer needle having a sharp distal tip. At least the inner surface of the distal portion of the catheter tightly engages the outer surface of the needle to prevent peelback of the catheter and thus facilitate insertion of the catheter into the blood vessel. The catheter and the introducer needle are assembled so that the distal tip of the introducer needle extends beyond the distal tip of the catheter with the bevel of the needle facing up away from the patient's skin. The catheter and introducer needle are generally inserted at a shallow angle through the patient's skin into a blood vessel.

In order to verify proper placement of the needle and/or catheter in the blood vessel, the clinician generally confirms that there is "flashback" of blood in a flashback chamber of the catheter assembly. Once proper placement of the catheter into the blood vessel is confirmed, the clinician may apply pressure to the blood vessel by pressing down on the patient's skin over the blood vessel distal of the introducer needle and the catheter. This finger pressure occludes the vessel, minimizing further blood flow through the introducer needle and the catheter.

The clinician may then withdraw the introducer needle from the catheter. The introducer needle may be withdrawn into a needle tip shield device that covers the needle tip and prevents accidental needle sticks. In general, a needle shield includes a housing, a sleeve, or other similar device that is designed such that when the needle is withdrawn from the patient, the needle tip will be trapped/captured within the needle tip shield. The purpose of these needle tip shield devices is to house the tip of the needle in a secure location, thereby avoiding the possibility of needle sticks after the needle and needle shield device are separated from the catheter, which is left in place to provide intravenous access to the patient.

Various systems and methods are available that are designed to shield needle tips and then be separated from the remainder of a catheter assembly following catheterization. Some currently available tip shield systems locate the tip shield within the catheter assembly, thereby exposing various surfaces of the needle shield to blood present within the catheter assembly. Upon removal of the tip shield from the catheter assembly, blood may be flicked or splattered, thereby exposing the clinician to blood and blood borne pathogens. Accordingly, there is a need in the art for a catheter assembly having tip shielding features that overcomes the failings of present devices. Such a catheter assembly is provided herein.

BRIEF SUMMARY OF THE INVENTION

The present invention has been developed in response to problems and needs in the art that have not yet been fully resolved by currently available vascular access systems and methods. Thus, these systems and methods are developed to provide more efficient vascular access systems and methods capable of ensuring proper needle tip shield function.

An extravascular system for accessing the vasculature of a patient may include a catheter adapter having a distal end supporting a catheter, and further comprising a proximal opening, wherein the catheter adapter includes a lumen extending therebetween. The extravascular system further includes a blood control septum disposed within the lumen of the catheter adapter and dividing the lumen into a proximal fluid chamber and a distal fluid chamber. In some instances, an extravascular system is provided having a septum activator slidably positioned within the proximal fluid chamber, wherein the septum activator includes a base and a probe end. The system further includes an external safety mechanism removably coupled to the proximal opening of the catheter adapter and comprising a safety clip configured to secure a sharpened tip of an introducer needle.

Some implementations of the present invention further include an external safety mechanism having a needle shield housing a safety clip that is configured to retain a sharpened tip of the introducer needle within the needle shield. The external safety mechanism may also include a needle hub having a first end for securing a proximal end of the introducer needle, and a second end configured to temporarily house the needle shield, wherein the needle shield is slidably housed within the second end. The needle hub may be temporarily coupled to the catheter adapter and configured to support an introducer needle, the introducer needle extending outwardly from the needle hub and through the catheter adapter, septum activator, blood control septum and catheter.

In some instances, the present invention includes a safety clip having a pawl or other structural feature configured to prevent the sharpened tip of the introducer needle from exiting a distal opening of the needle shield. The safety clip may also be configured to selectively interconnect the needle shield and the catheter adapter. In some instances, the external safety mechanism is configured to be removed from the proximal opening of the catheter adapter following removal of the sharpened tip of the introducer needle from the catheter and catheter adapter.

Some implementations of the present invention further include a tether that is configured to couple the needle shield to the needle hub. The tether includes a first end coupled to the needle hub and a second end coupled to the needle shield, the tether having a length that provides a maximum distance between the needle hub and the needle shield, wherein the maximum distance positions and retains the sharpened tip within the needle shield. Some implementations of the present invention further include a blood control septum having a self-sealing or self-closing opening, such as a slit. The blood control septum is further configured to control a flow of a fluid through the catheter adapter. The blood control septum may be activated or opened to selectively permit passage of fluids through the lumen of the catheter adapter.

Other implementations of the present invention comprise a catheter adapter having a proximal opening that is configured to receive a Luer adapter. Some embodiments include a proximal opening having a structural feature configured to receive a Luer adapter, such as a set of threads or a detent.

Some implementations of the present invention further include a septum activator or actuator that is configured to be selectively advanced through the blood control septum, to provide a fluid pathway therethrough. In some instances, the septum activator comprises a base configured to contact a Luer adapter that is inserted within the proximal opening of the catheter adapter. The septum activator is slidably inserted within the catheter adapter and configured for advancement through the blood control septum when contacted and advanced in a distal direction by the Luer adapter. The septum activator further comprises a pathway through which the introducer needle passes, and wherein the pathway provides fluid communication between the proximal and distal fluid chambers when the septum activator is advanced through the blood control septum.

Some implementations of the present invention further include a safety clip that is moveable between a first position and a second position, wherein the first position permits passage of the sharpened tip through a distal opening of the external safety mechanism, and the second position prevents passage of the sharpened tip through the distal opening of the external safety mechanism.

Some implementations of the present invention further include an access port that is coupled to, or forms a portion of the catheter adapter. The access port comprises an inner lumen that may be accessed via a needleless connector, such as a syringe or Luer adapter. The catheter adapter further includes a defeatable barrier that is seated within an annular groove formed on the inner surface of the catheter adapter and forms a sealed interface with the inner lumen of the access port. In some instances, the defeatable barrier is placed in the catheter adapter an immobilized solely via a friction fit. The defeatable barrier is defeated by inserted an external device into the inner lumen of the access port, whereby the external device contacts and temporarily defeats the barrier. In other instances, fluid pressure from the external device builds up within the access port until the barrier is defeated and the fluid is allowed to bypass the barrier and flow into the lumen of the catheter adapter. Once defeated, fluid communication is provided between the inner lumen of the access port and the lumen or fluid pathway of the catheter adapter. Upon removal of the external device, the resilient nature of the defeatable barrier causes the barrier to resume its tubular shape, thereby reestablishing its sealed interface with the inner lumen of the access port. The sealed interface prevents active fluid communication between the inner lumen and the lumen of the catheter adapter. In some instances, the defeatable barrier comprises a non-tubular shape or configuration.

Some implementations of the present invention include a method for manufacturing an extravascular system, wherein the method includes steps for: 1) providing a catheter adapter having a distal end supporting a catheter, and further comprising a proximal opening, the catheter adapter having a lumen; 2) disposing a blood control septum within the lumen of the catheter adapter, the blood control septum dividing the lumen into a proximal fluid chamber and a distal fluid chamber; 3) slidably positioning a septum activator within the proximal fluid chamber, the septum activator having a base and a probe end; and 4) removably coupling an external safety mechanism to the proximal opening of the catheter adapter, the external safety mechanism having a safety clip that is configured to secure a sharpened tip of an introducer needle.

These and other features and advantages of the present invention may be incorporated into certain embodiments of the invention and will become more fully apparent from the following description and appended claims, or may be learned by the practice of the invention as set forth hereinafter. The present invention does not require that all the advantageous features and all the advantages described herein be incorporated into every embodiment of the invention.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

DETAILED DESCRIPTION OF THE INVENTION

The presently preferred embodiments of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Figure 1:
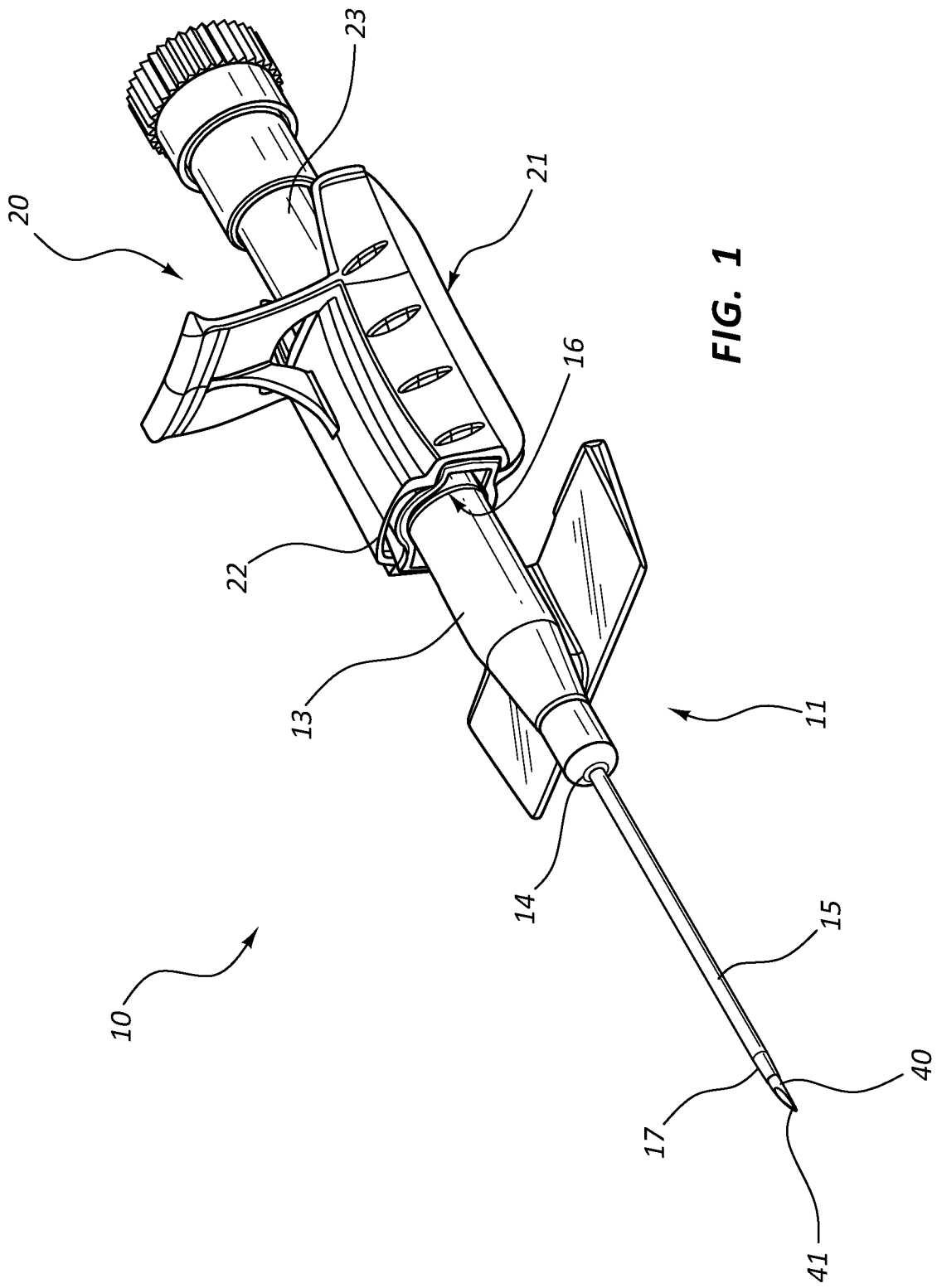
FIG. 1 is a perspective view of a catheter assembly in accordance with a representative embodiment of the present invention.

Referring to FIG. 1, a perspective view illustrates an example of an extravascular system 10 incorporating an external safety mechanism. In this example the extravascular system 10 includes a catheter assembly 11 and an external safety mechanism comprising a needle assembly 20. The catheter assembly 11 includes a catheter adapter 13 having a distal end 14 configured to support an intravenous catheter 15. Intravenous catheter 15 is configured for insertion into the vasculature of a patient, and therefore may comprise any length and diameter sufficient to access a desired vein or artery of the patient. Catheter 15 may further comprise any material or combination of materials compatible for use with the vasculature of a patient. For example, in some embodiments catheter 15 comprises a polymer material, such as polyvinyl chloride, polypropylene, silicone, Teflon, nylon, and/or latex rubber.

Catheter adapter 13 further comprises a proximal end 16 having an opening whereby to access an interior lumen of catheter adapter 13. In some embodiments, proximal end 16 further comprises structural features to accommodate attachment of various Luer devices to catheter adapter 13. For example, in some embodiments proximal end 16 comprises a set of threads. Proximal end 16 is further configured to compatibly and selectively receive needle assembly 20.

Needle assembly 20 comprises a needle hub 21 having a distal opening 22 that is configured to compatibly and selectively receive proximal end 16 of catheter adapter 13. Needle hub 21 further comprises a distal end 23 that is configured to support and permanently retain a proximal end of an introducer needle 40. Introducer needle 40 further comprises a sharpened distal end 41 that is threaded through catheter adapter 13 and catheter 15 to provide extravascular system 10. Once fully assembled, sharpened distal end 41 of needle 40 extends distally beyond the tip 17 of catheter 15. As thus configured, sharpened distal end 41 is exposed and may be used to provide an opening through the skin and soft tissues of the patient, thus providing an opening through which tip 17 of catheter 15 may be inserted into the vasculature of the patient.

Figure 2:
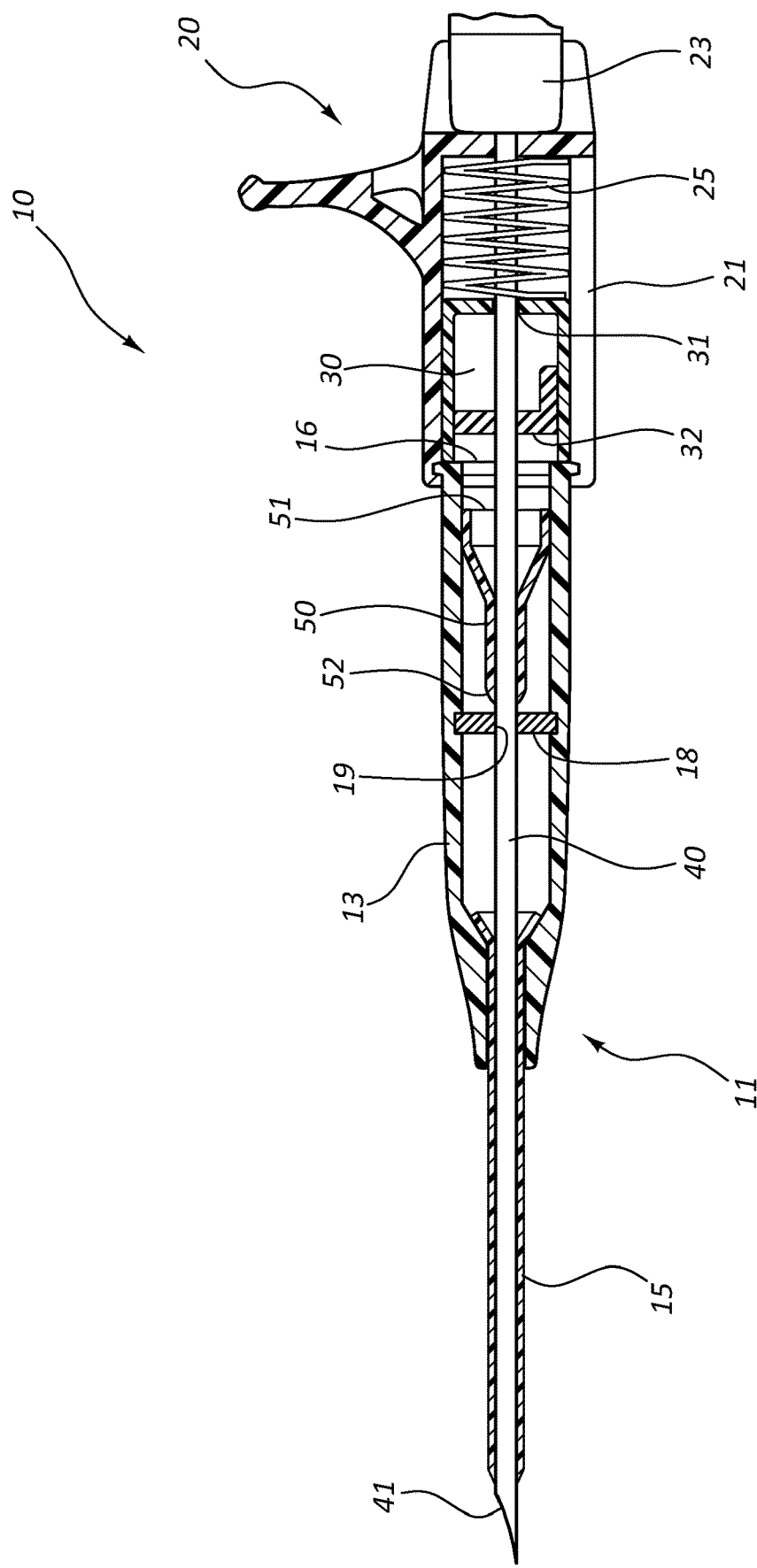
FIG. 2 is a cross-section view of a catheter assembly in accordance with a representative embodiment of the present invention.

Referring now to FIG. 2, catheter adapter 13 further comprises a blood control septum 18 that is positioned within an inner lumen of catheter adapter 13. Blood control septum 18 divides the inner lumen of catheter adapter 13 into proximal and distal fluid chambers, wherein blood control septum 18 prevents fluid communication between the fluid chambers. In some instances, blood control septum 18 comprises a self-sealing slit 19 or small opening through which introducer needle 40 is inserted when assembled. Upon removal of needle 40 from catheter adapter 13, slit 19 automatically closes, thereby preventing fluid communication between the fluid chambers. Thus, blood control septum 18 prevents fluid within the catheter 15 and the distal fluid chamber from entering the proximal fluid chamber and leaking out of catheter adapter 13 via the opening in proximal end 16.

Catheter adapter 13 further comprises a septum activator 50 that is configured to be slidably advanced through blood control septum 18, thereby providing a fluid pathway through septum 18. Septum activator 50 is slidably positioned within the proximal fluid chamber. Septum activator 50 comprises a base 51 that is oriented towards proximal end 16 and is accessible via proximal end 16. Septum activator 50 further comprises a probe end 52 that is oriented towards, and proximal to blood control septum 18. Septum activator 50 is advanced through blood control septum 18 by inserting a Luer device through the opening of proximal end 16, as will be discussed in greater detail below.

Septum activator 50 may comprise any material or combination of materials that are compatible for use in an intravenous device. Generally, septum activator 50 comprises a rigid material. For example, in some embodiments septum activator 50 comprises a nylon material. Septum activator 50 may further comprise an antibacterial coating or anticoagulant coating to provide further benefits to the extravascular assembly 10.

With continued reference to FIG. 2, needle assembly 20 further comprises a needle shield 30 that is slidably stored in a distal opening of needle hub 21. Needle shield 30 comprises a proximal aperture 31 through which introducer needle 40 is threaded. Needle shield 30 further comprises a needle clip 32 that is configured to block distal movement of sharpened tip 41 when positioned within needle shield 30.

In some embodiments, needle shield 30 is coupled to needle hub 21 via a tether 25. Tether 25 is configured to permit needle shield 30 to be slid distally along introducer needle 40, but prevents needle shield 30 from being completely removed from needle 40, as shown in FIG. 3.

Figure 3:
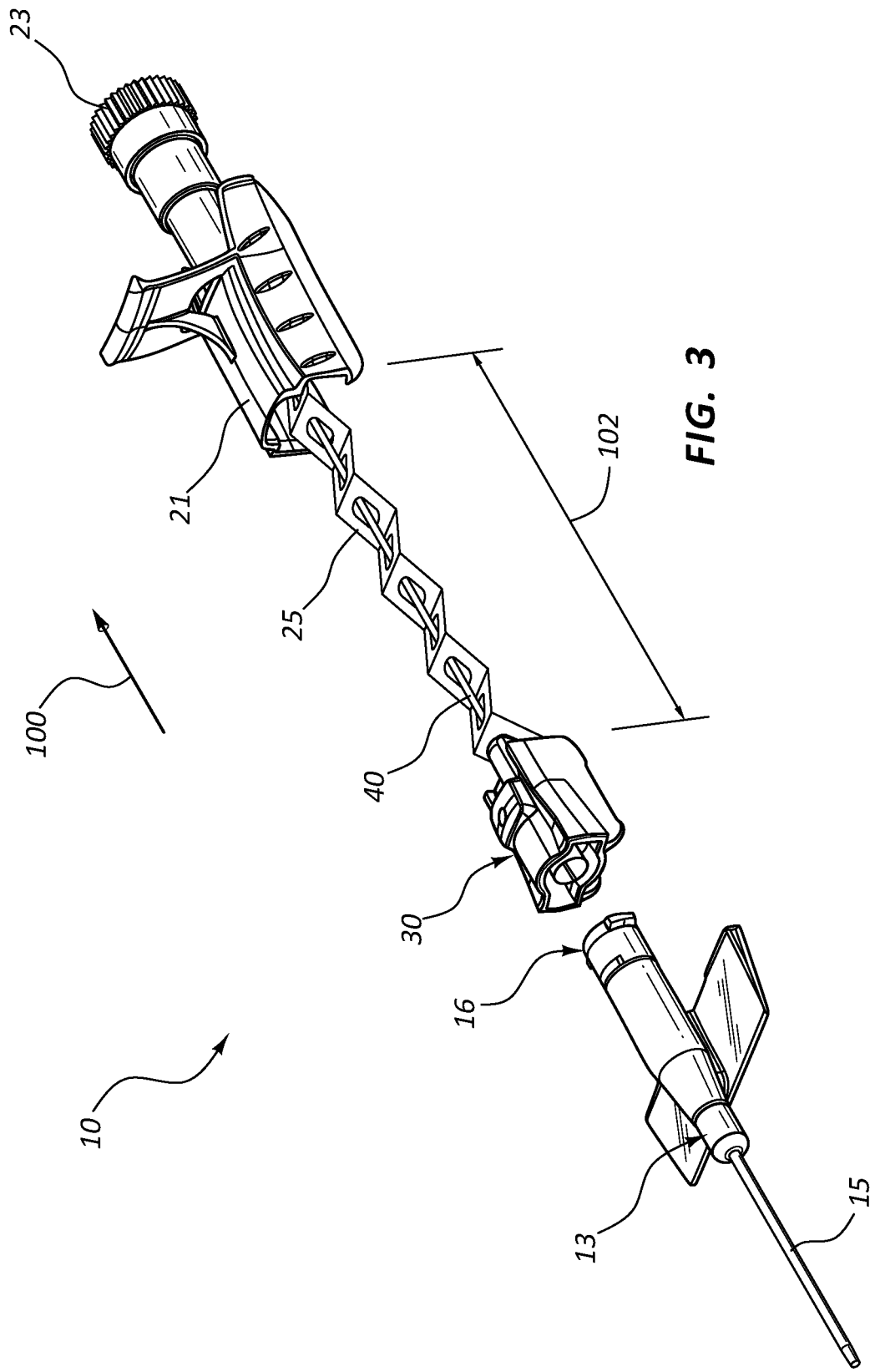
FIG. 3 is an exploded view of the catheter assembly of FIG. 1 in accordance with a representative embodiment of the present invention.
Figure 4:
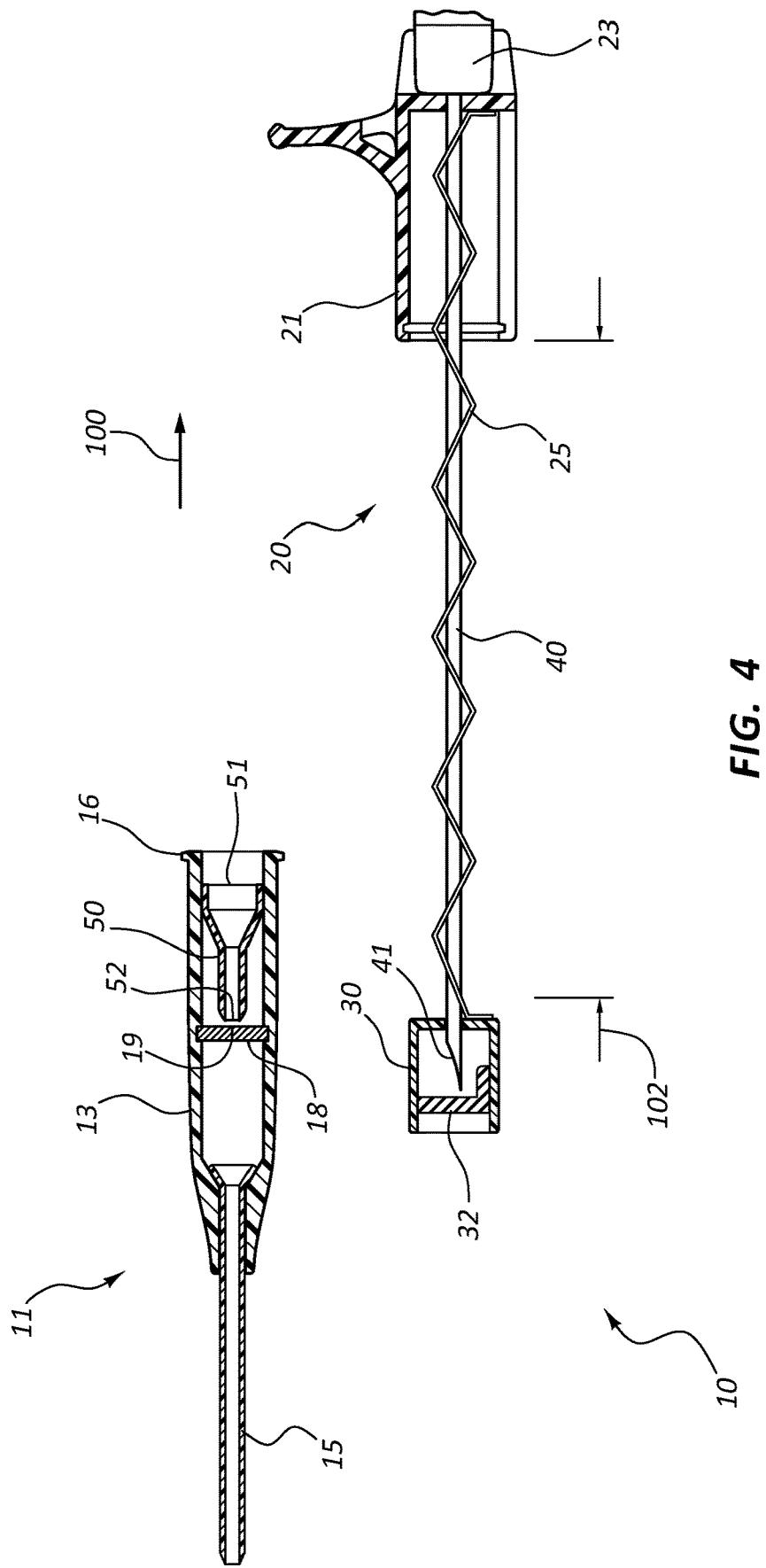
FIG. 4 is a cross-section view of a catheter assembly following separation of the needle shield assembly from the catheter adapter in accordance with a representative embodiment of the present invention.

Referring now to FIGS. 3 and 4, extravascular system 10 is shown in an expanded configuration, which represents the configuration of the various components following a catheterization procedure. The catheterization procedure results in catheter 15 being inserted into the vasculature of a patient. Once catheter 15 is properly inserted into the patient's vasculature, needle hub 21 is moved in proximal direction 100 thereby removing needle shield 30 from the distal opening of needle hub 21. Introducer needle 40 and sharpened tip 41 are withdrawn from catheter 15 and catheter adapter 13 as needle hub 21 is moved in proximal direction 100.

Tether 25 is unraveled from the distal opening of needle hub 21 as needle hub 21 moves in proximal direction 100, as shown in FIG. 4. When a maximum distance 102 between needle hub 21 and needle shield 30 is achieved, tether 25 prevents further separation or distance between the two components. Sharpened tip 41 is entirely withdrawn from catheter adapter 13 and into needle shield 30 at a distance that is less than maximum distance 102.

In some embodiments, safety clip 32 is repositioned within needle shield 30 to block and prevent sharpened tip 41 from exiting needle shield 30 once tip 41 has been drawn proximally past safety clip 32, as shown in FIG. 4. Thus, sharpened tip 41 is trapped within needle shield 30. In particular, needle shield 30 prevents sharpened tip 41 from exiting the distal end of needle shield 30, and tether 25 prevents sharpened tip 41 from exiting the proximal end of needle shield 30 by preventing separation of needle shield 30 and needle hub 21 in excess of maximum distance 102.

In some embodiments, safety clip 32 is further configured to securely retain the connection between needle shield 30 and catheter proximal end 16 of catheter adapter 13. In some instances, safety clip 32 further comprises a pawl or other feature that selectively and/or temporarily interconnects with a surface of proximal end 16 when safety clip 32 is held in a first position. The first position of safety clip 32 is maintained by contact between introducer needle 40 and safety clip 32. When introducer needle 40 is withdrawn past safety clip 32 in proximal direction 100, safety clip 32 is released from the first position and is repositioned to block sharpened tip 41 from exiting needle shield distally. When safety clip 32 is repositioned, the pawl or other feature releases the surface of proximal end 16, thereby permitting physical separation of catheter adapter 13 from needle shield 30, as shown.

Figure 5:
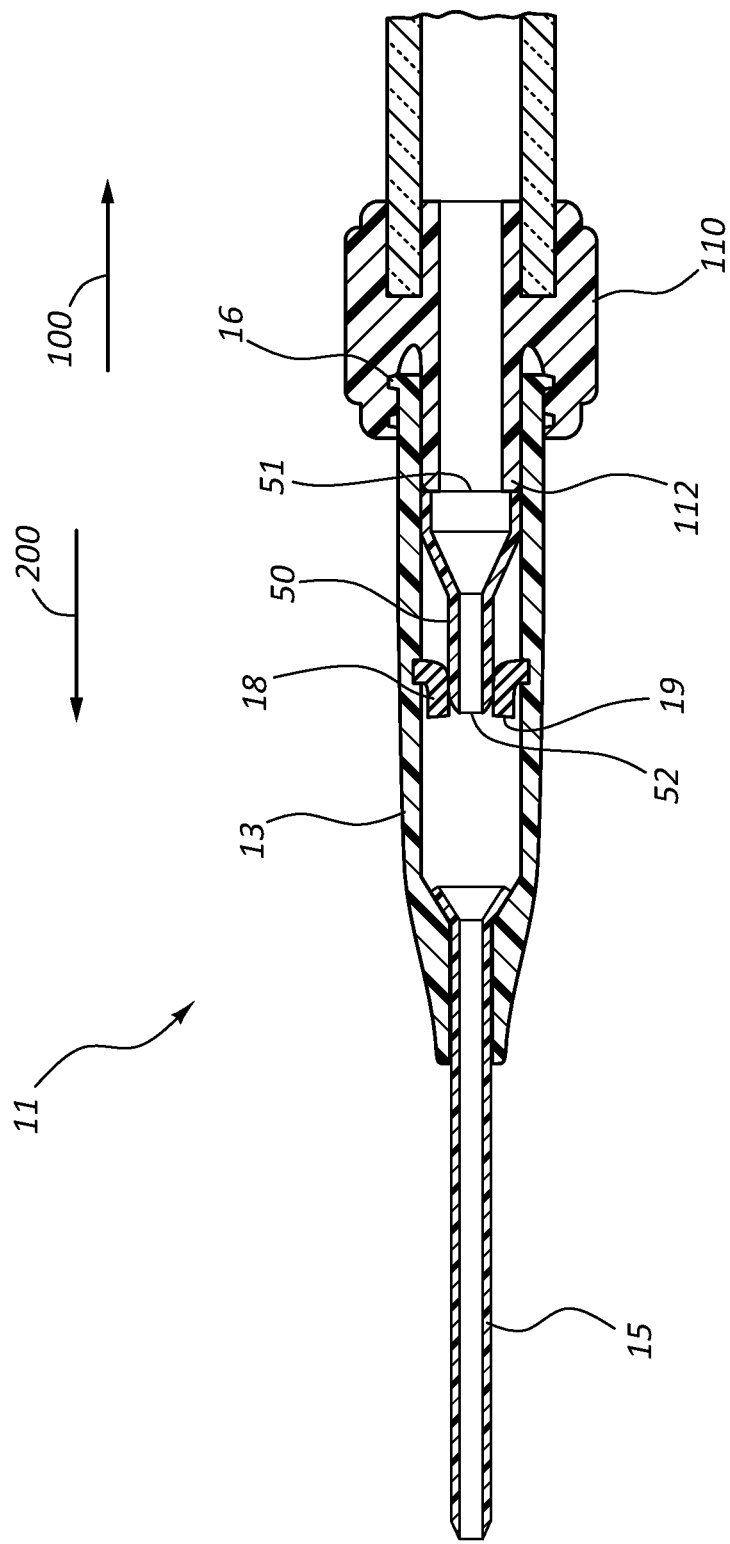
FIG. 5 is a cross-section view of a catheter assembly coupled to a Luer device, wherein the septum activator is advanced through the blood control septum in accordance with a representative embodiment of the present invention.
Figure 6A:
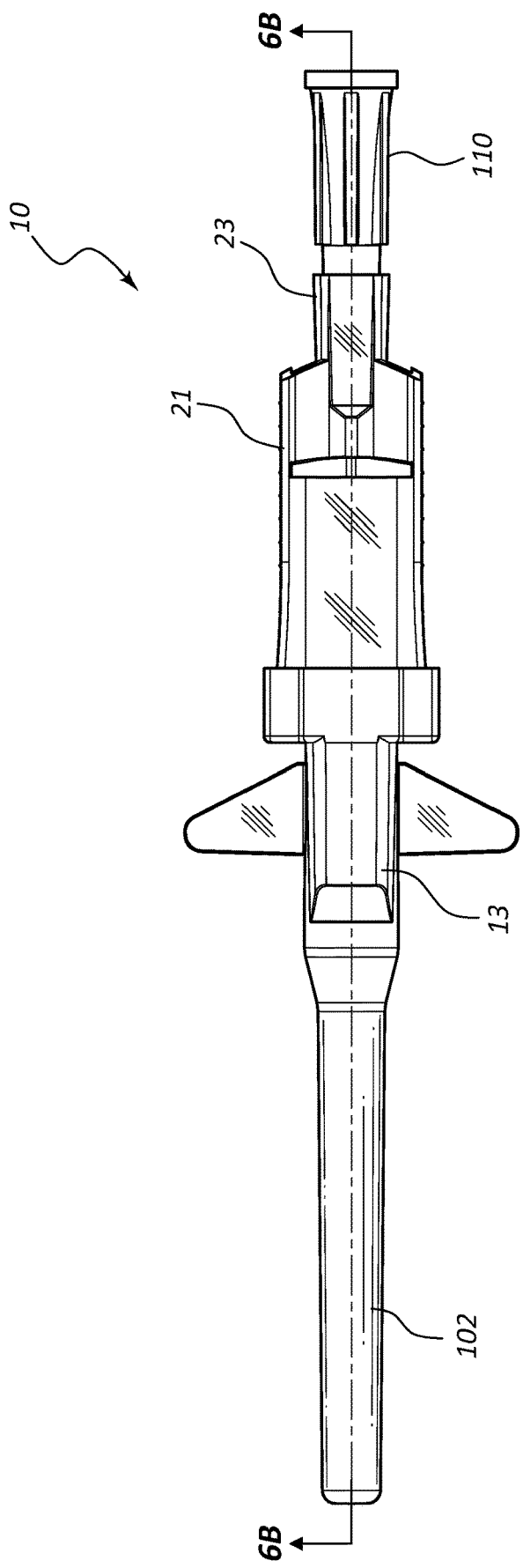
FIG. 6, shown in parts A-H, provides various plan and cross-section views of an extravascular access device in accordance with a representative embodiment of the present invention.
Figure 6B:
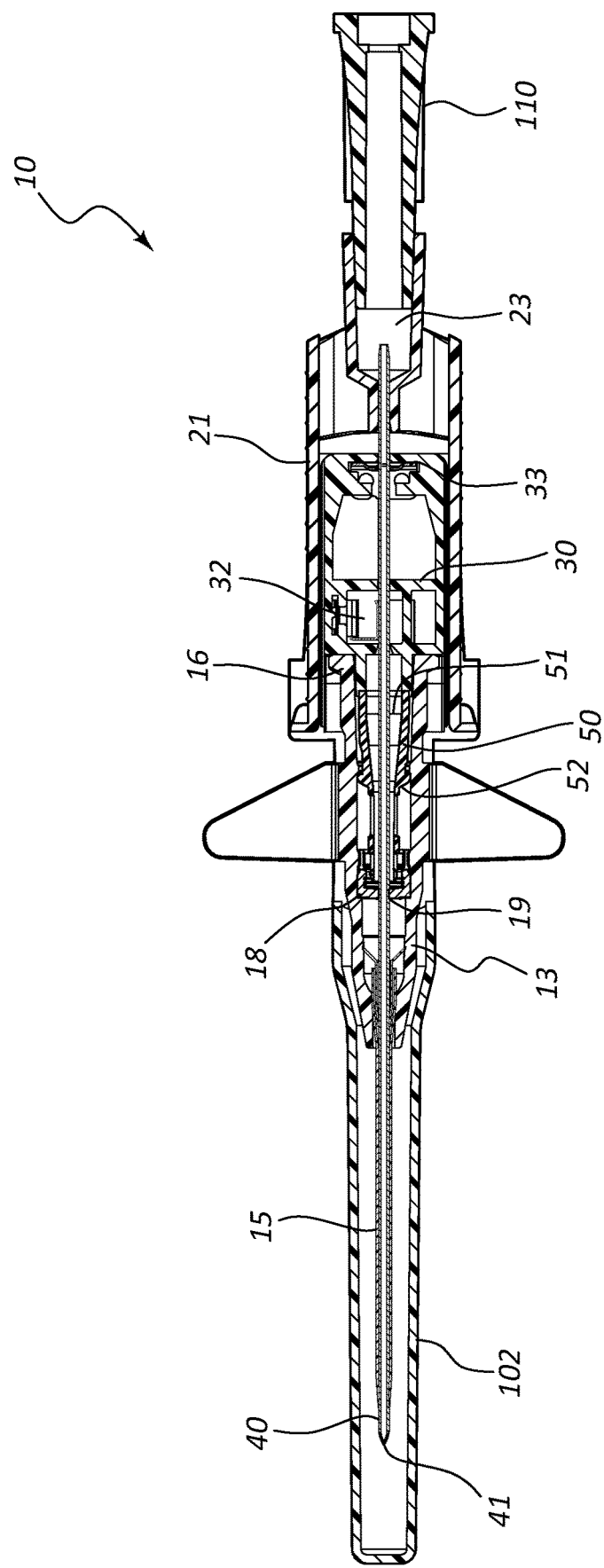
Figure 6C:
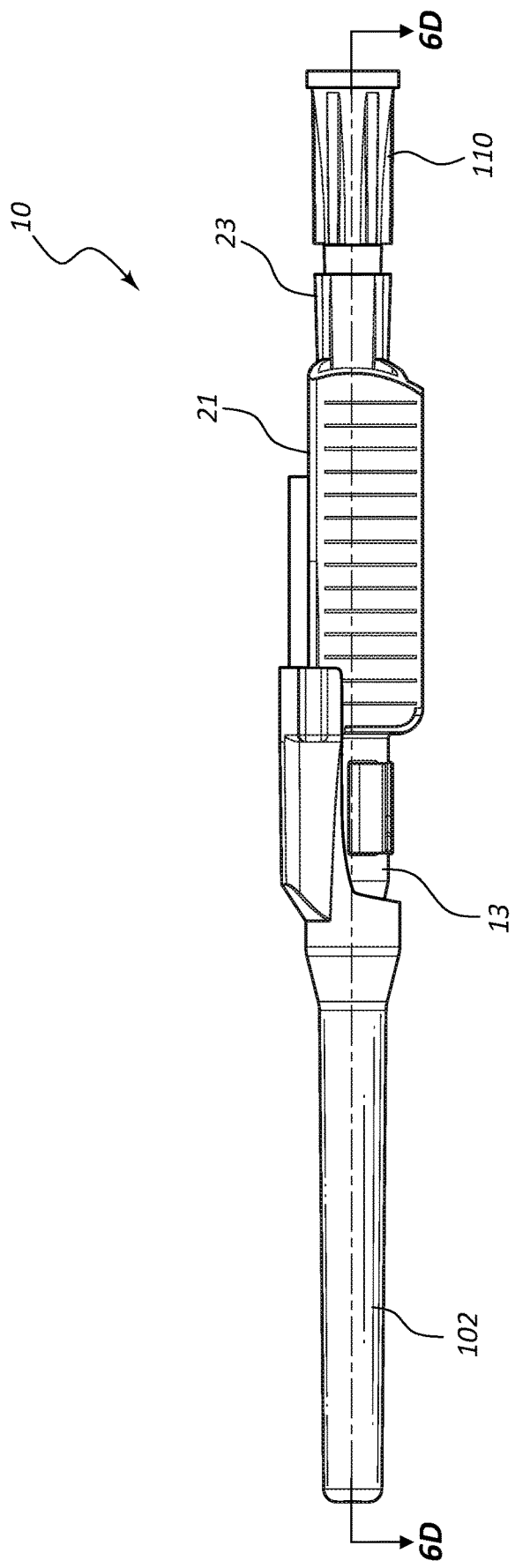
Figure 6D:
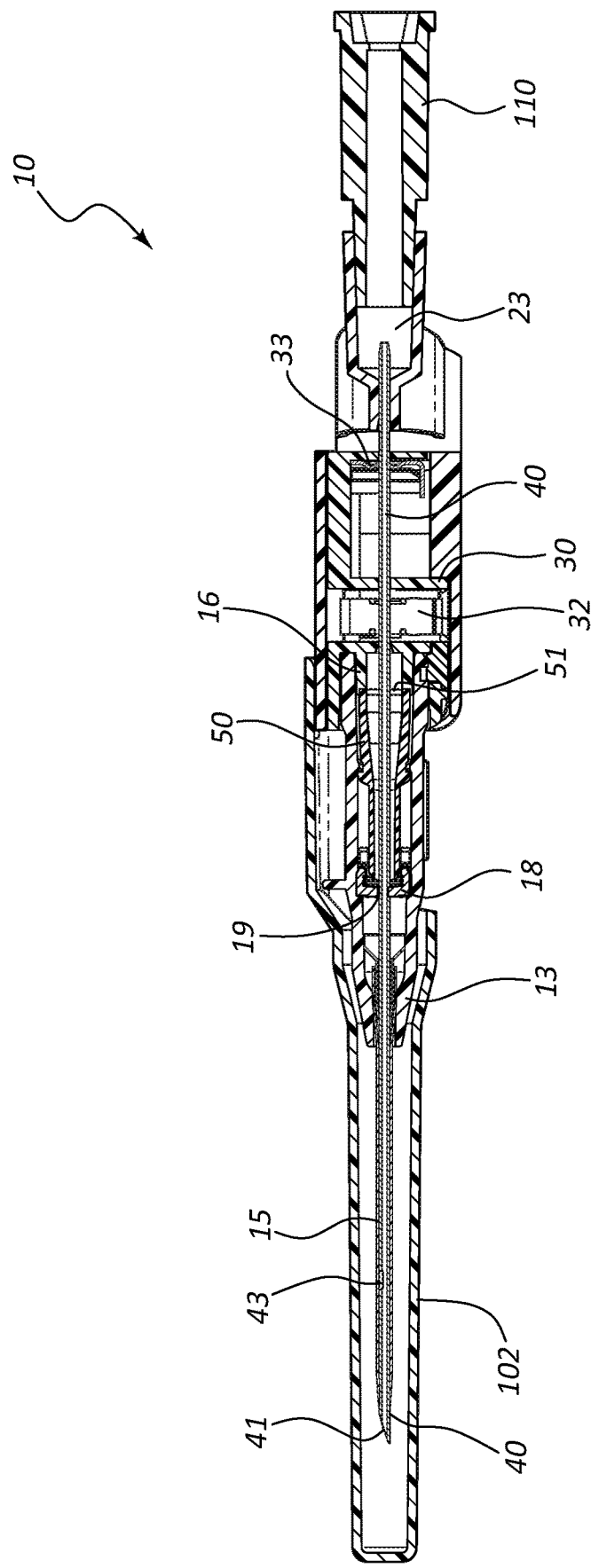
Figure 6E:
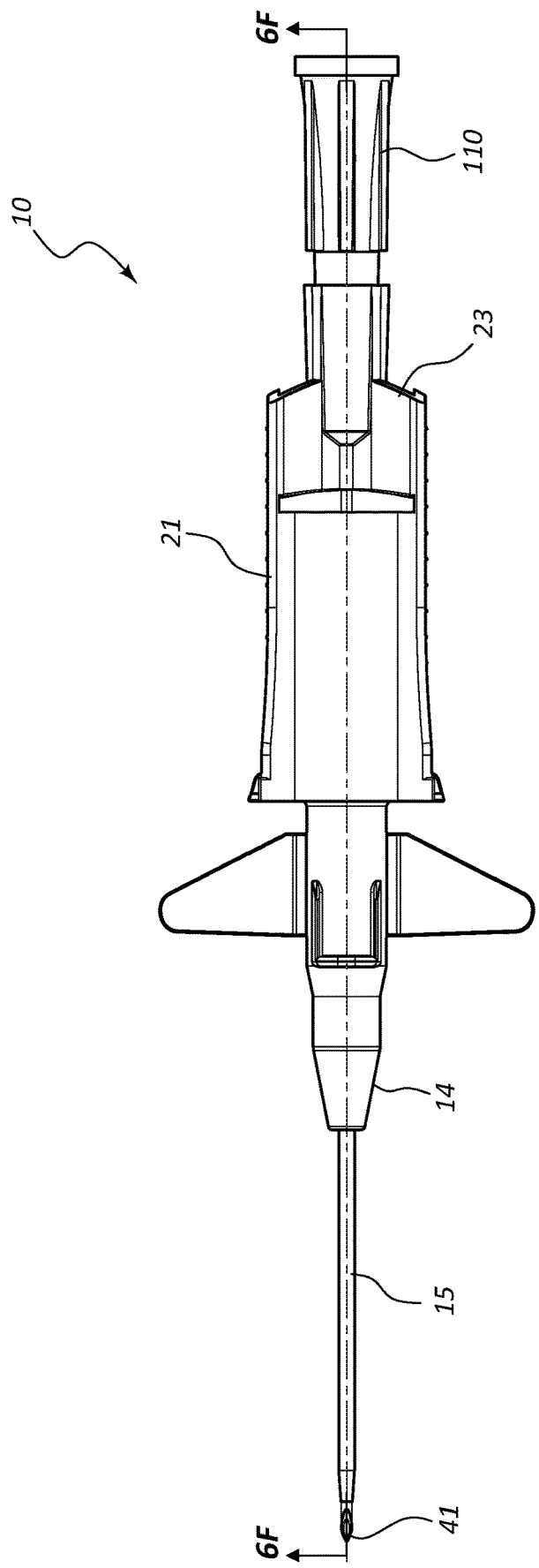
Figure 6F:
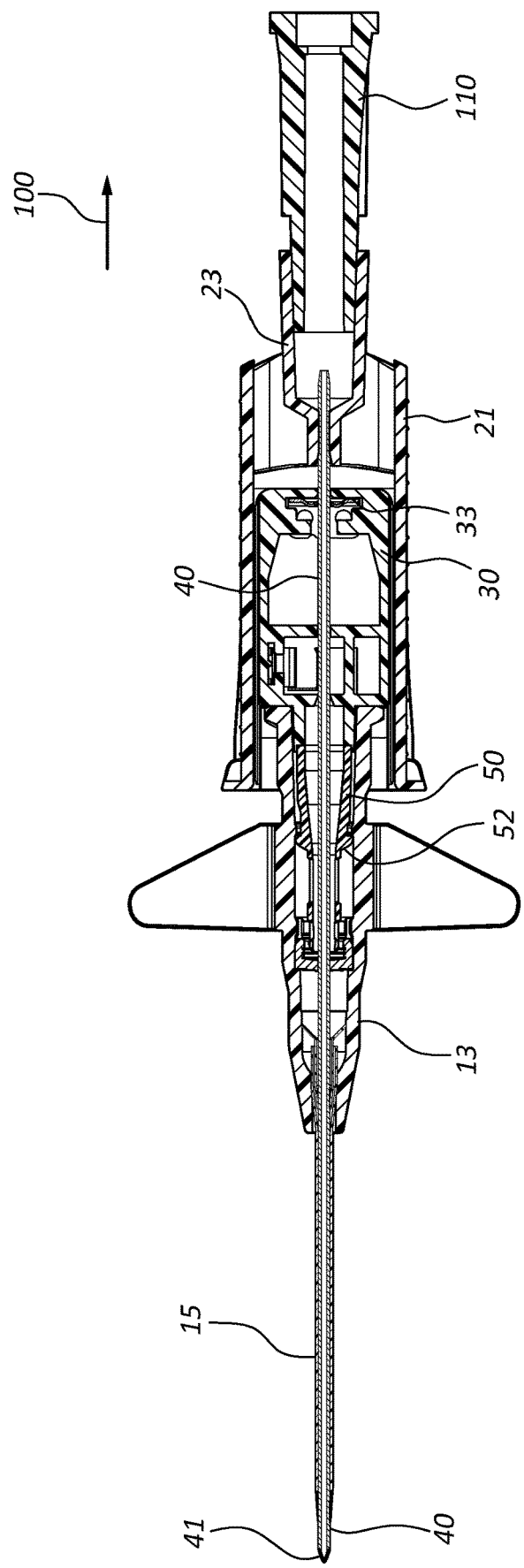
Figure 6G:
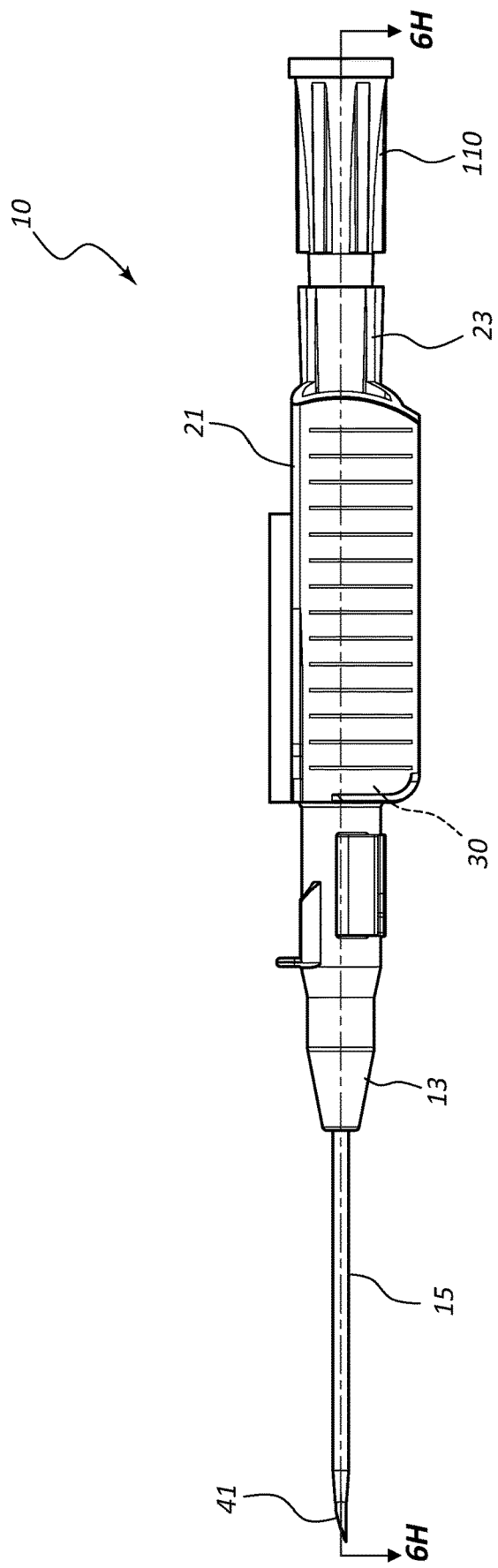
Figure 6H:
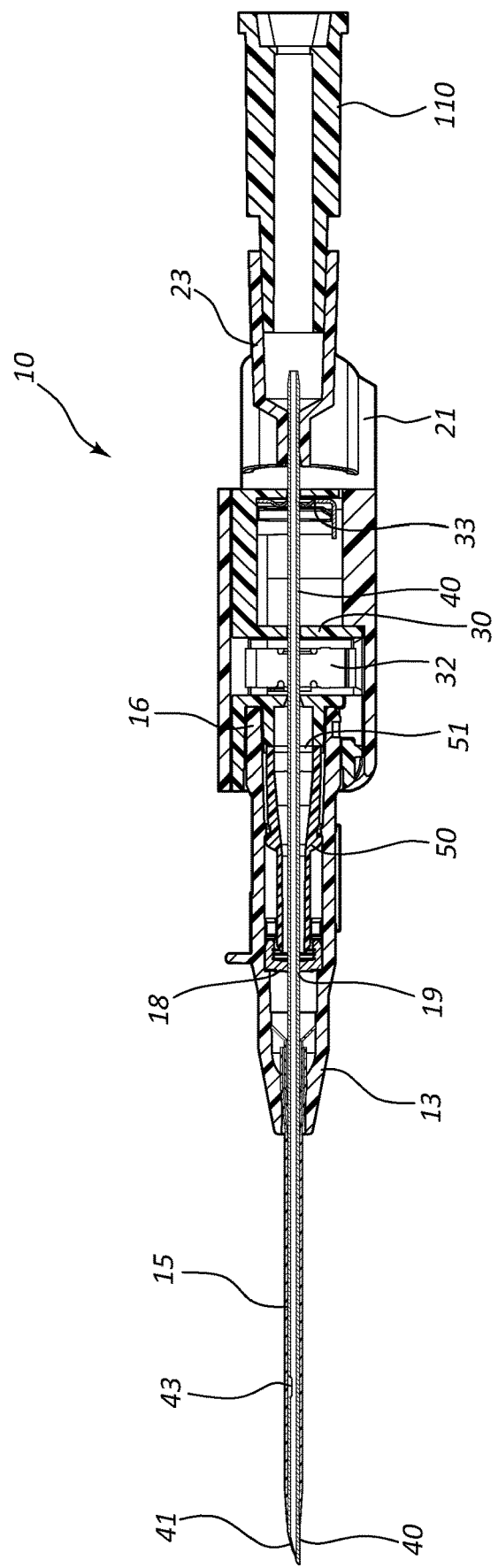
Figure 7A:
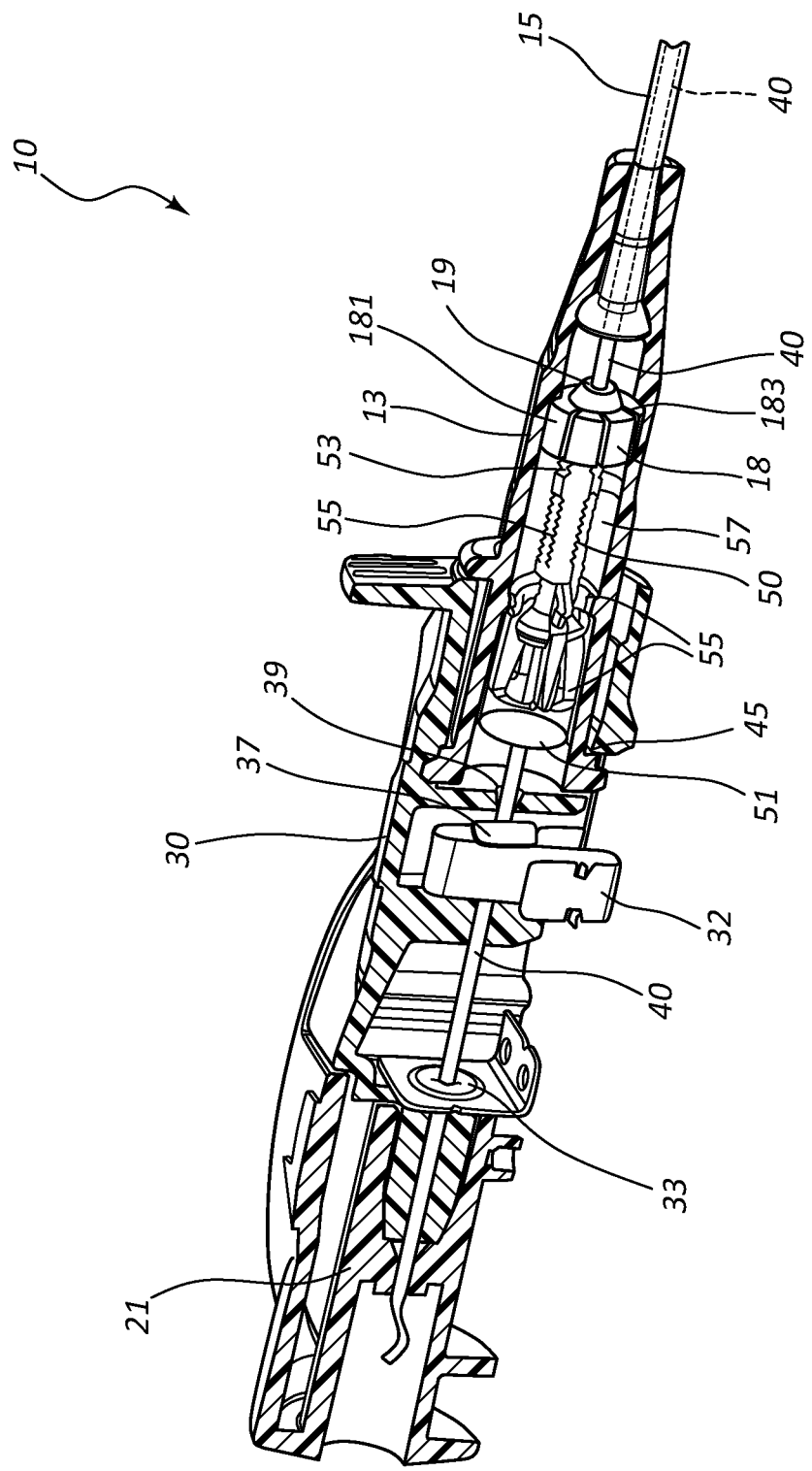
FIG. 7, shown in parts A-E, provides various views of an extravascular access device in accordance with a representative embodiment of the present invention.
Figure 7B:
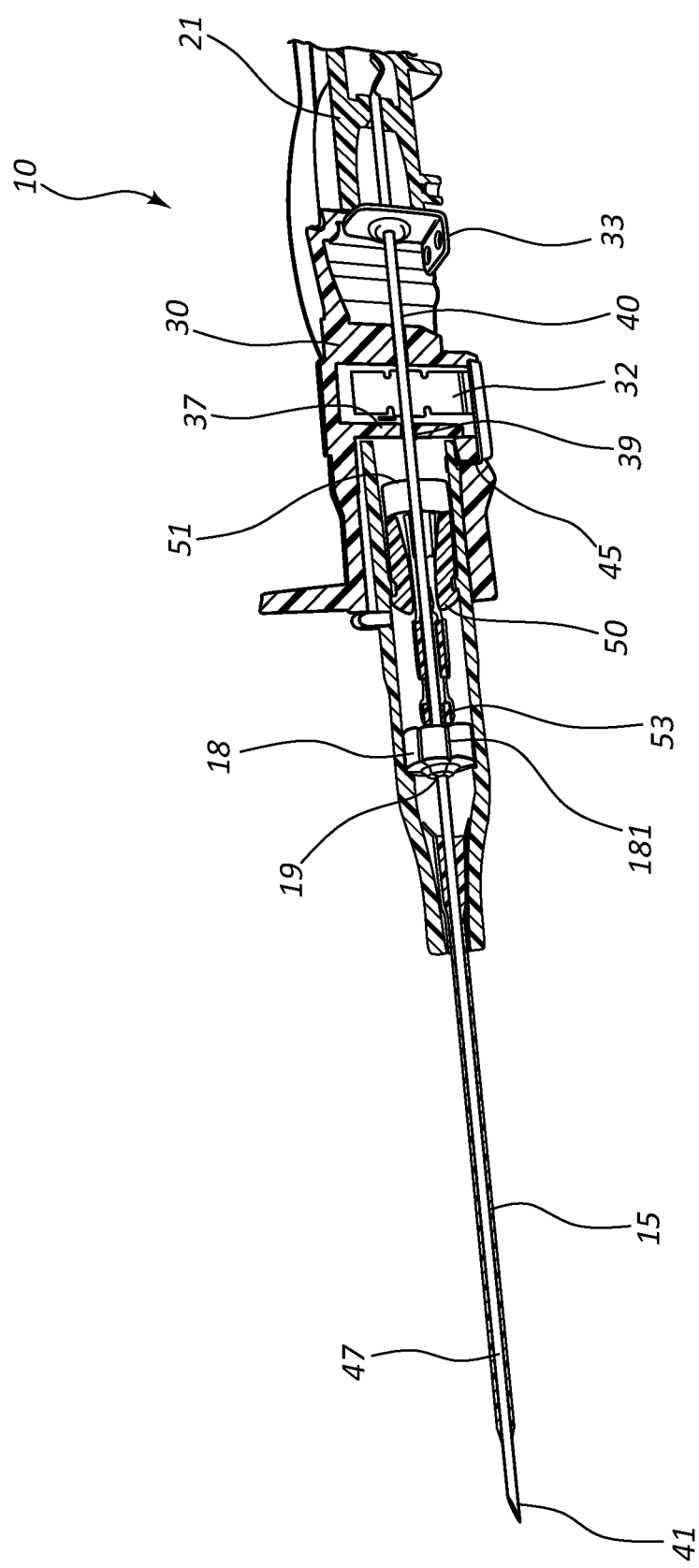
Figure 7C:
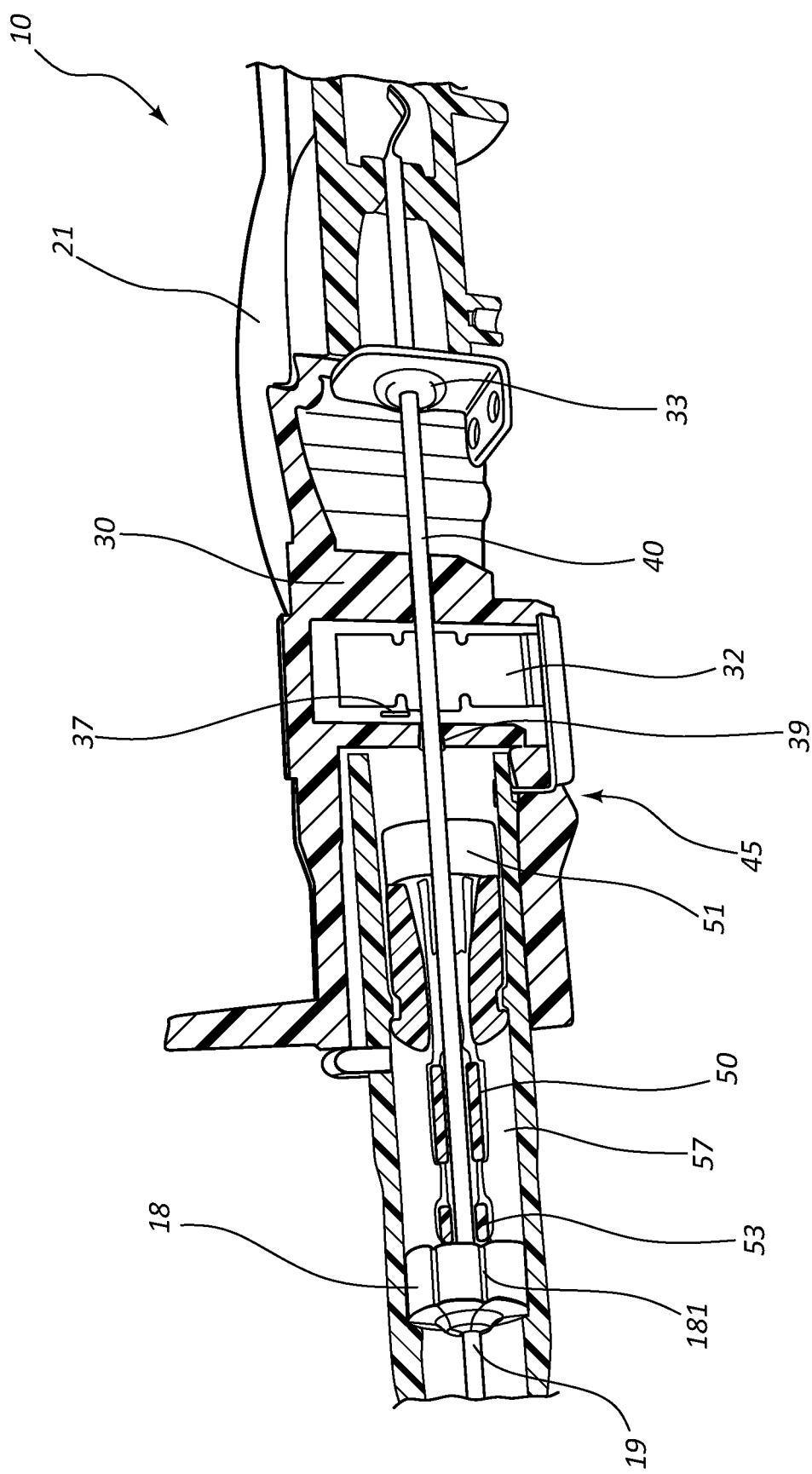
Figure 7D:
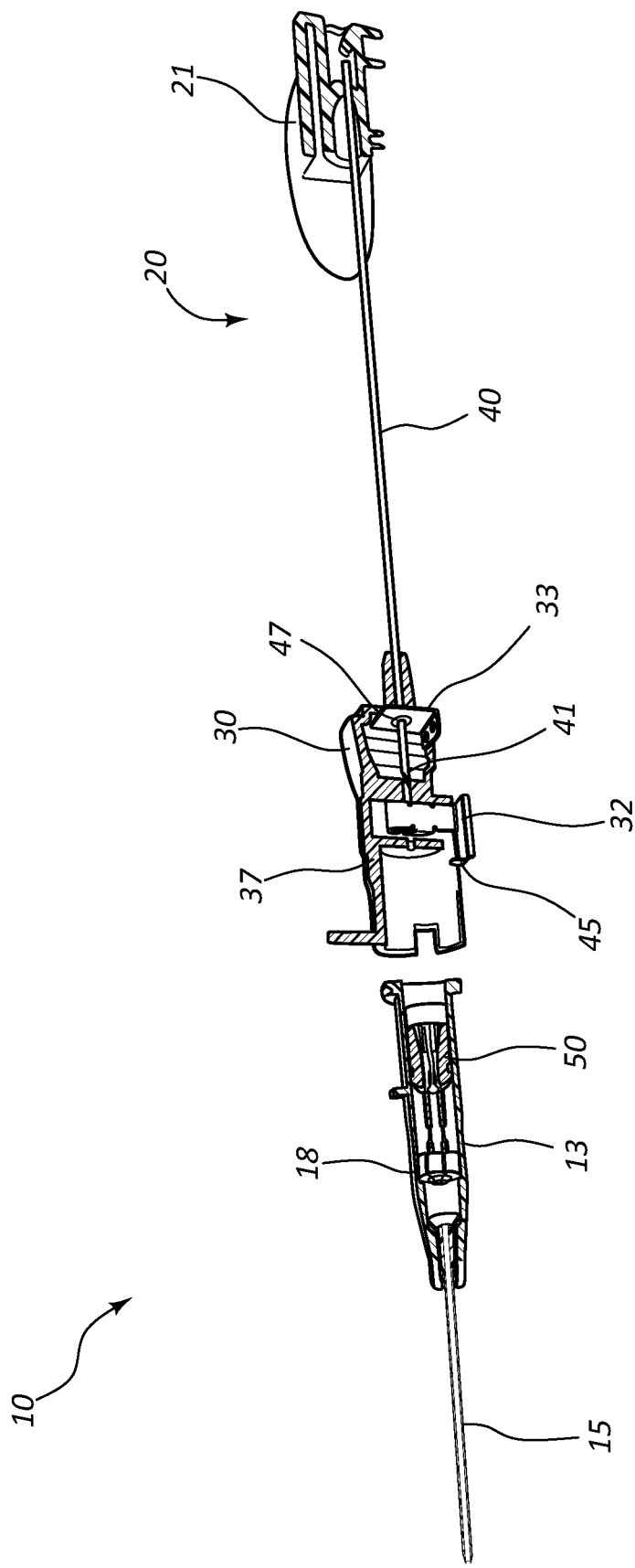

Referring now to FIG. 5, catheter adapter 13 is shown following separation from needle shield 30. In some embodiments, the vasculature of a patient is accessed via catheter assembly 11 by inserting a Luer adapter 110 or other device into the proximal end or opening 16 of catheter adapter 13. In some instances, Luer adapter 110 comprises a probe 112 that is inserted within opening 16 and contacts base 51 of septum activator 50. Upon insertion of probe 112 into opening 16, probe 112 contacts septum activator 50 and advances septum activator 50 within the proximal fluid chamber in distal direction 200. Upon further insertion of probe 112 into opening 16, probe end 52 of septum activator is advanced through slit 19 of blood control septum 18, thereby providing fluid communication between Luer adapter 110 and catheter 15 via the distal fluid chamber.

Some embodiments of the present invention provide a single use septum activator, wherein the septum activator maintains a pathway through the blood control septum following removal of a Luer device from the catheter adapter. In other embodiments, the present invention provides a multiple use septum activator, wherein the septum activator is automatically removed from the blood control septum following removal of a Luer device from the catheter adapter, thereby closing a pathway through the blood control septum.

For example, in some embodiments upon removal of Luer adapter 110 from proximal end 16, septum activator 50 is moved in proximal direction 100 as slit 19 of septum 18 resumes its closed position. Thus, fluid in the distal fluid chamber and catheter 15 are prevented from bypassing septum 18 when Luer adapter 110 is disconnected. In other embodiments, upon removal of Luer adapter 110 from proximal end 16, septum activator 50 remains positioned within slit 19 of septum 18, thereby maintaining a fluid pathway through septum 18.

The various components and parts disclosed herein may comprise any shape or configuration that may be desired or necessary to achieve the benefits of the present invention. For example, needle shield 30 may achieve integrated tip protection using a transverse barrier containing a washer-like hole in the proximal end of safety clip 32 to catch a feature on the exterior surface of introducer needle 40, such as a crimp or a ferrule. Safety clip 32 may alternatively be divided into two or more pieces. For example, a first piece of clip 32 may provide the interlocking action between the needle shield 30 and catheter adapter 13. The second piece of clip 32 may provide the function of blocking sharpened tip 41 from exiting needle shield 40 in distal direction 200. Alternatively, the second piece of clip 32 may comprise a hole having a diameter that is greater than an outer diameter of needle 40, yet less than an outer diameter of a feature on the outer surface of the needle 40. As such, the second piece of clip 32 may prevent complete separation of needle shield 30 from needle 40, thereby trapping sharpened tip 41 within needle shield 30. Clip 32 may further include a non-friction coating to reduce drag forces on needle 40 when withdrawing needle 40 from catheter adapter 13 in proximal direction 100.

In some instances, blood control septum 18 further comprises various air vents and other features to permit controlled flashback in catheter 15 during catheterization. For example, in some embodiments catheter adapter 13 comprises a recessed surface configured to receive and retain septum 18. In some instances, the recessed surface further comprises a plurality of grooves that form air channels between the outer, circumferential surface of septum 18 and the recessed surface. Further, in some instances the plurality of grooves interconnect the distal and proximal fluid chambers, thereby permitting air pressure in the distal fluid chamber to be released into the proximal fluid chamber by passing through the plurality of grooves. As such, excess buildup of air pressure in the distal fluid chamber is prevented, thereby allowing blood to enter into the distal fluid chamber as flashback during catheterization. Alternatively, the outer, circumferential surface of septum 18 may comprises a plurality of grooves, thereby forming a plurality of air channels between the outer surface of the septum and the recessed surface of catheter adapter 13.

Referring now generally to FIGS. 6A-9B, various alternative and representative embodiments of the present invention are shown. In particular, FIGS. 6A-9B demonstrate various alternative configurations of extravascular system 10. FIGS. 6A-9B further demonstrate various alternative components and structures for extravascular system 10.

Referring now to FIGS. 6A-6H, an assembled extravascular system 10 is shown in various plan and cross-section views, prior to catheterization. In some instances catheter adapter 13 further comprises a needle cap 102 that is configured to receive and shield needle tip 41 and catheter 15 prior to use. Needle cap 102 comprises a proximal end that is friction fit over the distal end of catheter adapter 13. Prior to catheterization, needle cap 102 is removed from catheter adapter 13 and disposed.

In some instances, system 10 further comprises a flashback chamber 110 that is in fluid communication with the proximal end of introducer needle 40. Flashback chamber 110 comprises a clear material that is capable of being used with biological fluids, such as blood. Introducer needle 40 further comprises a window 43 that is positioned near sharpened distal tip 41. When sharpened tip 41 is inserted into the vasculature of the patient, blood flows through window 43 and into the space between the outer surface of needle 40 and the inner wall surface of catheter 15. This blood may be seen through the clear wall of the catheter, thereby providing a visual signal to the caregiver that the sharpened tip 41 is in the patient's vein. Excess blood travels through the hollow interior of introducer needle 40 and into flashback chamber 110. Flashback chamber 110 collects the excess blood, providing further confirmation of accurate needle and catheter placement into the vessel, and preventing undesired exposure to the caregiver. In some instances, flashback chamber 110 is coupled to needle hub 21 via a vented fitting whereby gas or air within flashback chamber 110 is vented as liquid enters from the proximal end and opening of needle 40.

In some instances, excess blood collected in flashback chamber 110 is preserved for clinical testing or other types of diagnostic procedures. For these instances, flashback chamber 110 may be selectively removed from needle hub 23 prior to disposal of needle 40 and the remaining disposable components of system 10.

In some embodiments, needle shield 30 comprises a washer 33 that forms the proximal aperture through which needle 40 is threaded. Needle 40 may further comprise a crimp or ferrule proximate to sharpened distal tip 41 that has a diameter that is greater than the diameter of the opening in washer 33. As such, the crimp or ferrule is prevented from passing through washer 33 in proximal direction 100. In some embodiments, the distance between sharpened tip 41 and the crimp or ferrule is configured so that sharpened tip 41 is entirely positioned within needle shield 30 when the crimp or ferrule contacts washer 33.

Referring now to FIGS. 7A-7E, various cross-section views of an extravascular system 10 is shown. In some embodiments, needle shield 30 comprises a clip 32 that is held in a compressed configuration by needle 40 prior to catheterization. When needle 40 is withdrawn from catheter 15 and tip 41 is drawn proximately past clip 32, clip 32 is released and flap or flag 37 covers and blocks aperture 39, thereby preventing sharpened distal tip 41 from exiting needle shield 30 via aperture 39. In some embodiments, clip 32 comprises a v-clip.

In some instances, a pawl 45 or other structure of clip 32 intersects and securely retains a portion of catheter adapter 13 when in the compressed configuration. For example, in some instances pawl 45 intersects the proximal rim of catheter adapter 13. When clip 32 is released following withdrawal of tip 41 into needle shield 30, pawl 45 of clip 32 releases catheter adapter 13, thereby permitting separation of the two components. Thus, needle shield 30 and catheter adapter 13 are securely interconnected prior to withdrawing distal tip 41, and capable of being separated once distal tip 41 is securely shielded within needle shield 30.

As discussed previously, in some embodiments blood control septum 18 comprises one or more air vents 181 which are formed in the outer circumferential surface of septum 18. Vents 181 provide a fluid and/or an air pathway between the inner surface of catheter adapter 13 and the outer surface of septum 18. Alternatively, air vents may be provided by grooving the inner surface of catheter adapter 13 at the position where septum 18 is seated.

Blood control septum 18 may further comprise blood wicking apertures 183 formed on distal face of the septum. Apertures 183 are positioned and configured to wick excess blood from the outer surface of introducer needle 40 when needle 40 is being withdrawn from catheter adapter 13. Apertures 183 may also wick excess blood that leaks into catheter adapter 13 as flashback during catheterization.

Septum activator 50 comprises a proximal end 51 that is configured to be contacted and advanced though slit or opening 19 of septum 18 when an external object is inserted into the proximal opening of catheter adapter 13. Septum activator 50 comprises a distal end 53 that is positioned proximate to septum 18, and is sized to permit partial or complete penetration of slit 19. In some instances, distal end 53 merely contacts and deforms septum 18, which thereby causes slit 19 to be biased into an open conformation.

In some instances, septum activator 50 is incapable of being removed from septum 18 following insertion through slit 19. Once inserted, septum activator 50 provides and/or opens a permanent pathway through septum 18. Thus, septum activator 50 may be configured for one-time use. In other instances, septum activator 50 is configured automatically be removed from or backed out of slit 19 when septum activator 50 is not actively advanced in distal direction 200, or held in place via an external device. For example, in some instances septum activator 50 is prevented from fully penetrating slit 19. Thus, when the external device is removed from catheter adapter 13, the elastic properties of septum 18 self-closes slit 19 thereby backing distal end 53 out of slit 19. Thus, septum activator 50 may be configured for multiple-time usage.

Septum activator 50 may further comprise one or more flow disrupting features 55. Features 55 are configured to provide disruption to fluid passing though catheter adapter 13 in proximity to septum activator 50. In some instances, septum activator 50 comprises one or more fins and/or windows 55 that divert fluid between the interior and exterior surfaces or surroundings of septum activator 50. Fins 55 may further be configured to slidably seat within an annular groove 57 on the inner surface of catheter adapter 13. The interaction between fins 55 and annular groove 57 prevents septum activator 50 from being removed from the proximal opening of catheter adapter 13. Annular groove 57 may also be configured to prevent over-insertion of distal end 53 through septum 18.

Figure 8A:
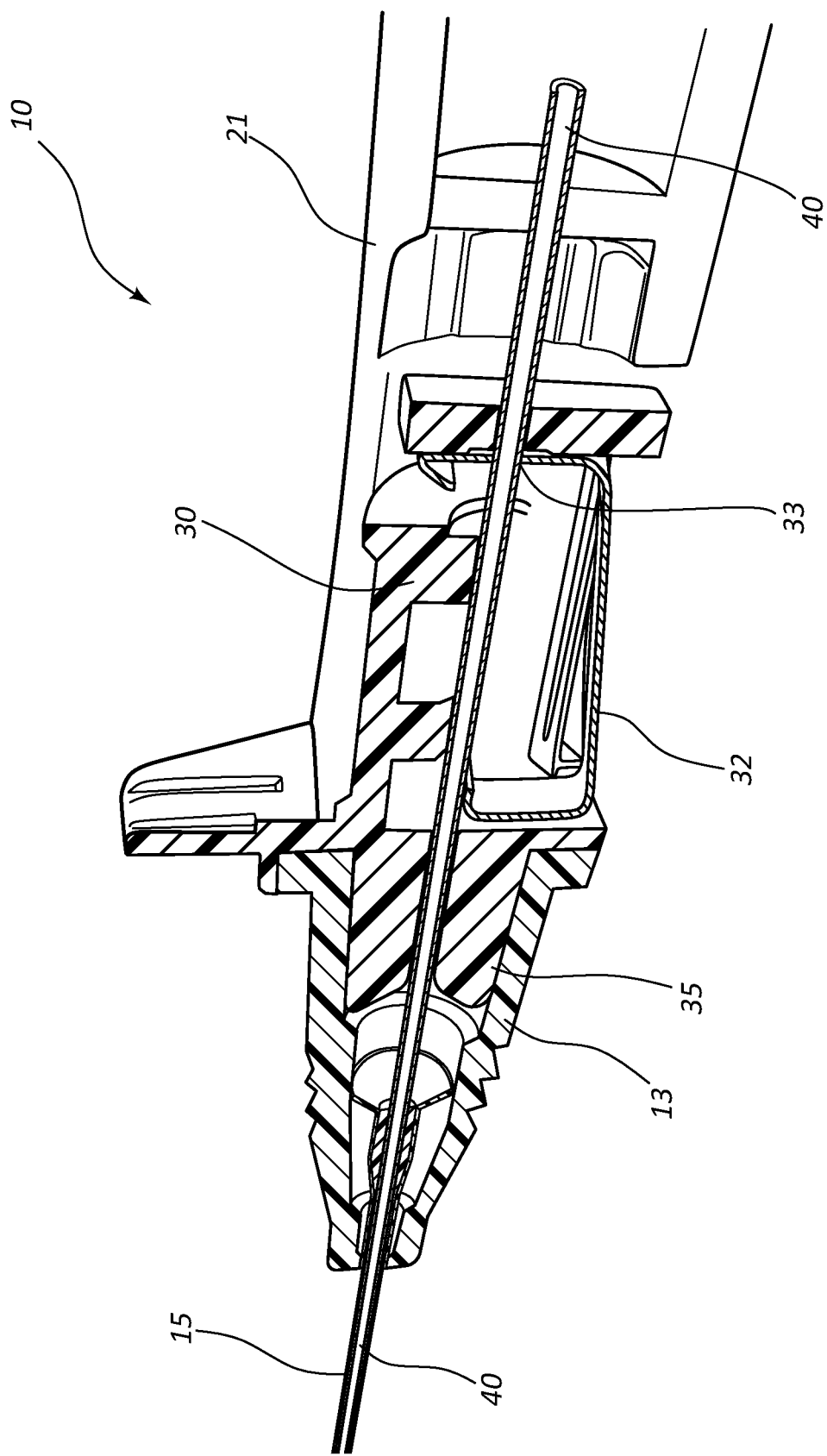
FIG. 8, shown in parts A-F, provides various views of an extravascular access device in accordance with a representative embodiment of the present invention.
Figure 8B:
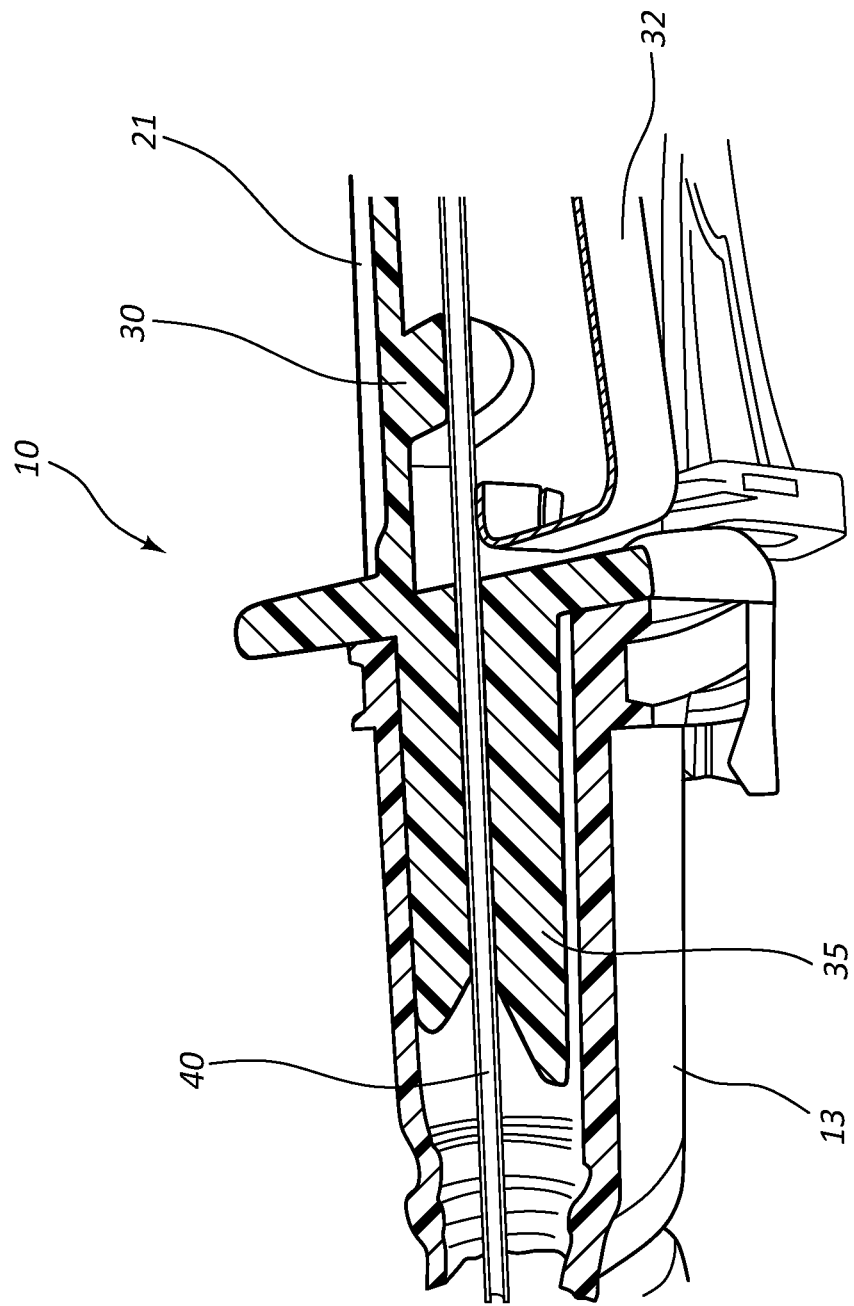
Figure 8C:
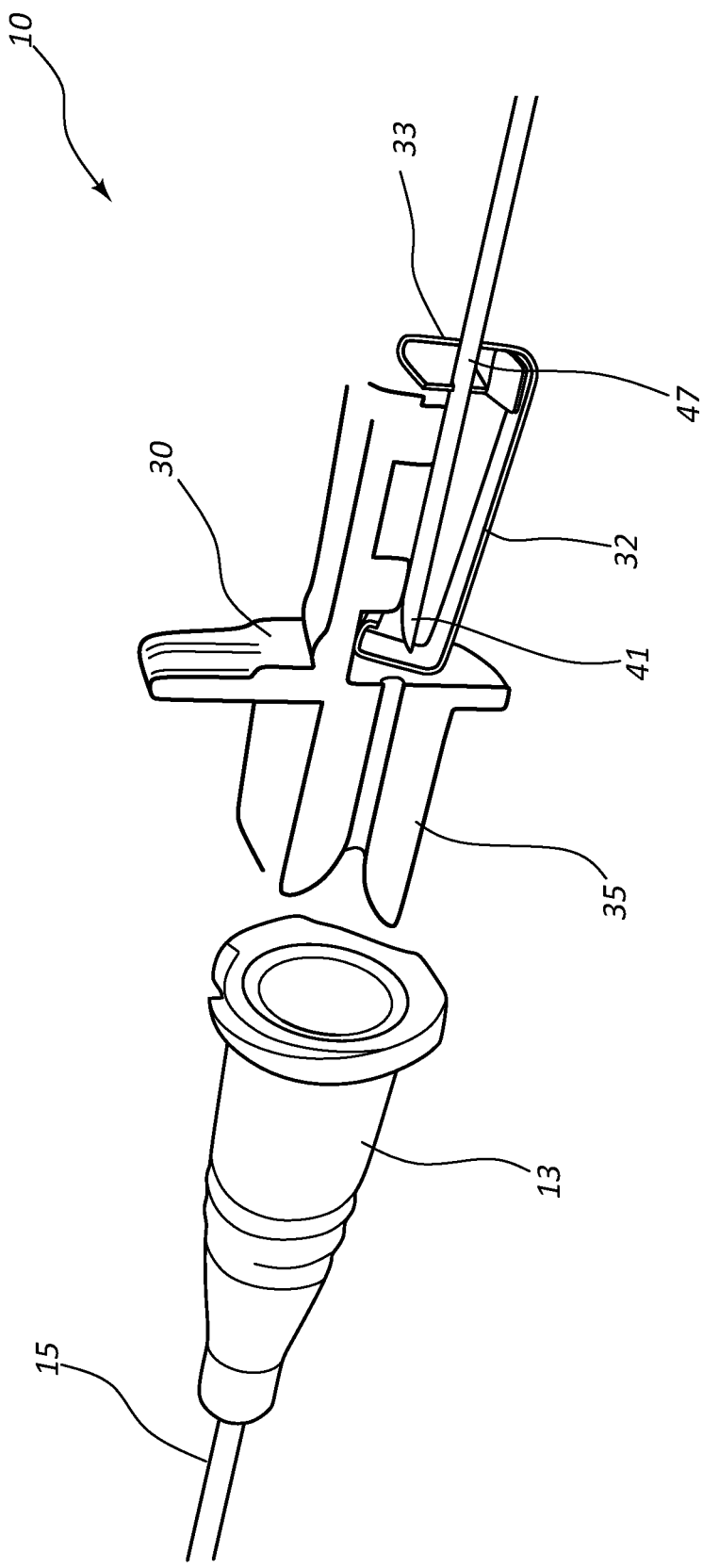
Figure 8D:
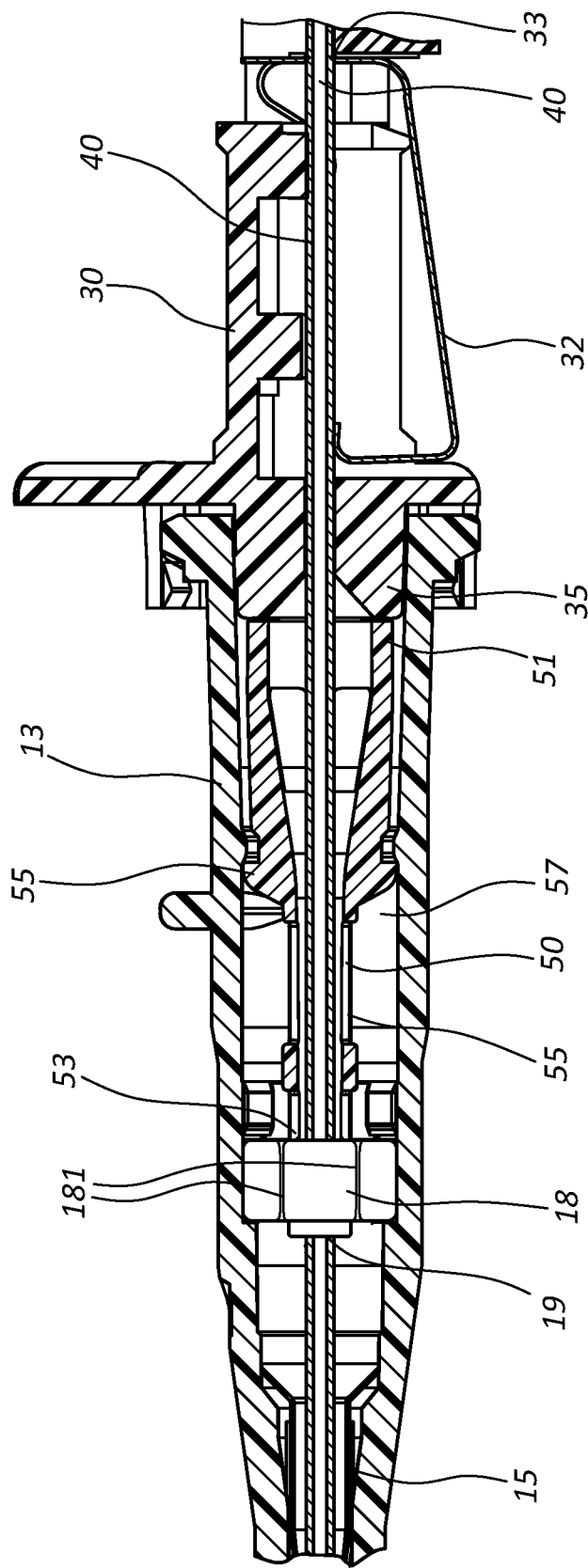
Figure 8E:
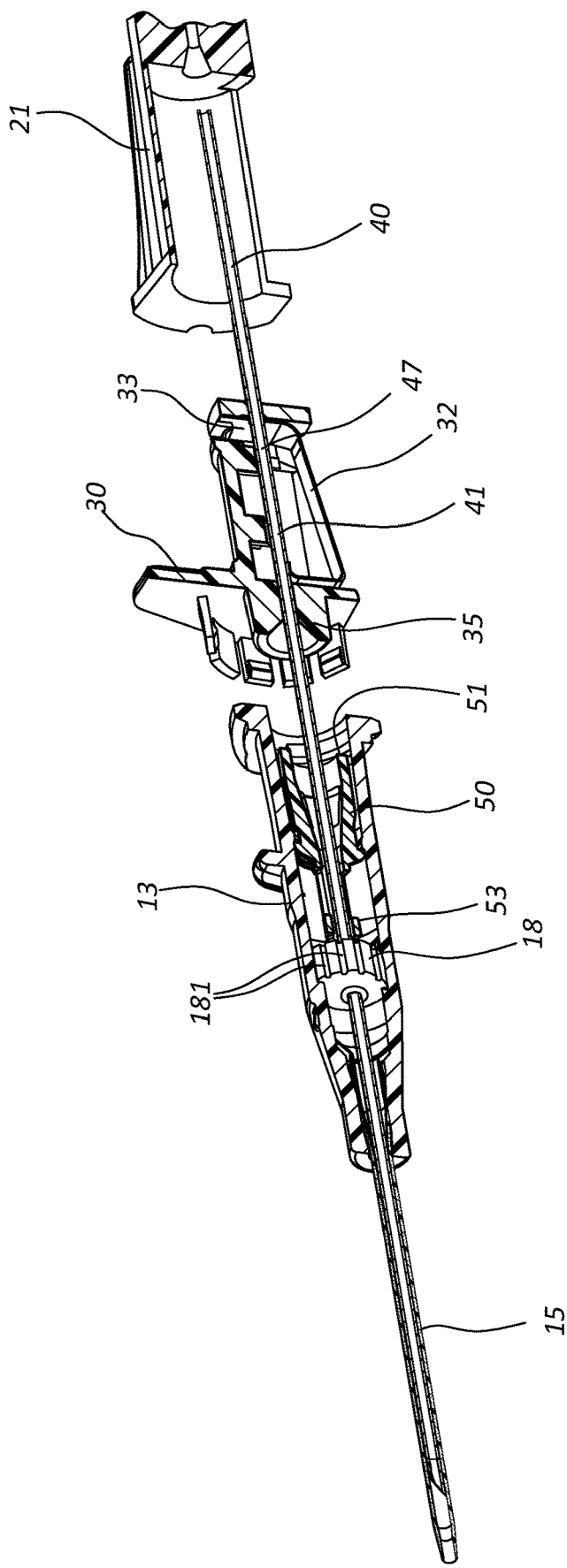
Figure 8F:
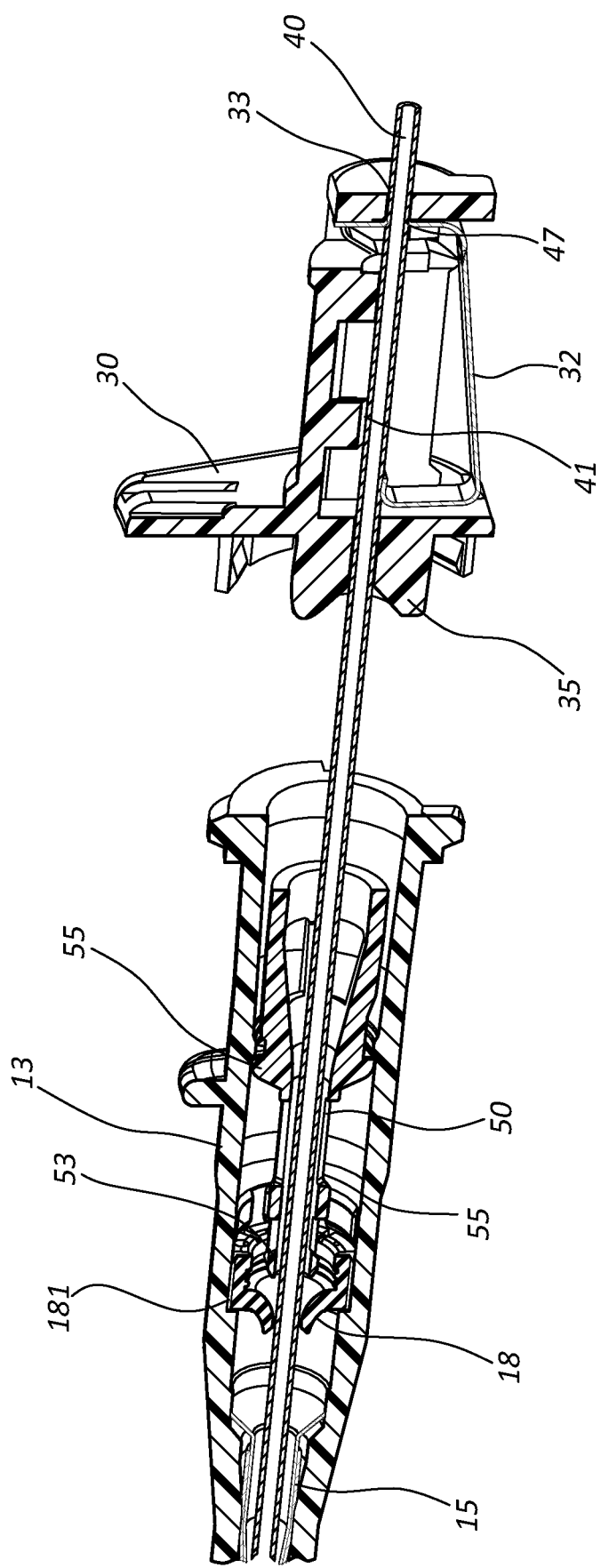

In some instances, needle shield 30 comprises a clip 32 having a distal end configured to block a distal aperture of shield 30, and further comprises a proximal end forming washer 33, as shown in FIGS. 8A-8C. The distal end of clip 32 is biased away from the distal aperture by the presence of needle 40 in the distal aperture. Following catheterization and withdrawal of distal tip 41 into needle shield 30, the distal end of clip 32 is released from its biased position and blocks the distal aperture, thereby preventing distal tip 41 from exiting safety shield 30. The aperture of washer 33 comprises a diameter that permits needle 40 to slide therethrough, but prevents passage of a crimp 47 or ferrule that is located on needle 40 proximate to distal tip 41. Thus the distal and proximal ends of clip 32 trap distal tip 41 within needle shield 30, as shown in FIG. 8C. Needle shield 30 may further comprise an extended distal nose 35 that securely and selectively interlocks needle shield 30 and catheter adapter 13 via a friction fit.

Figure 9A:
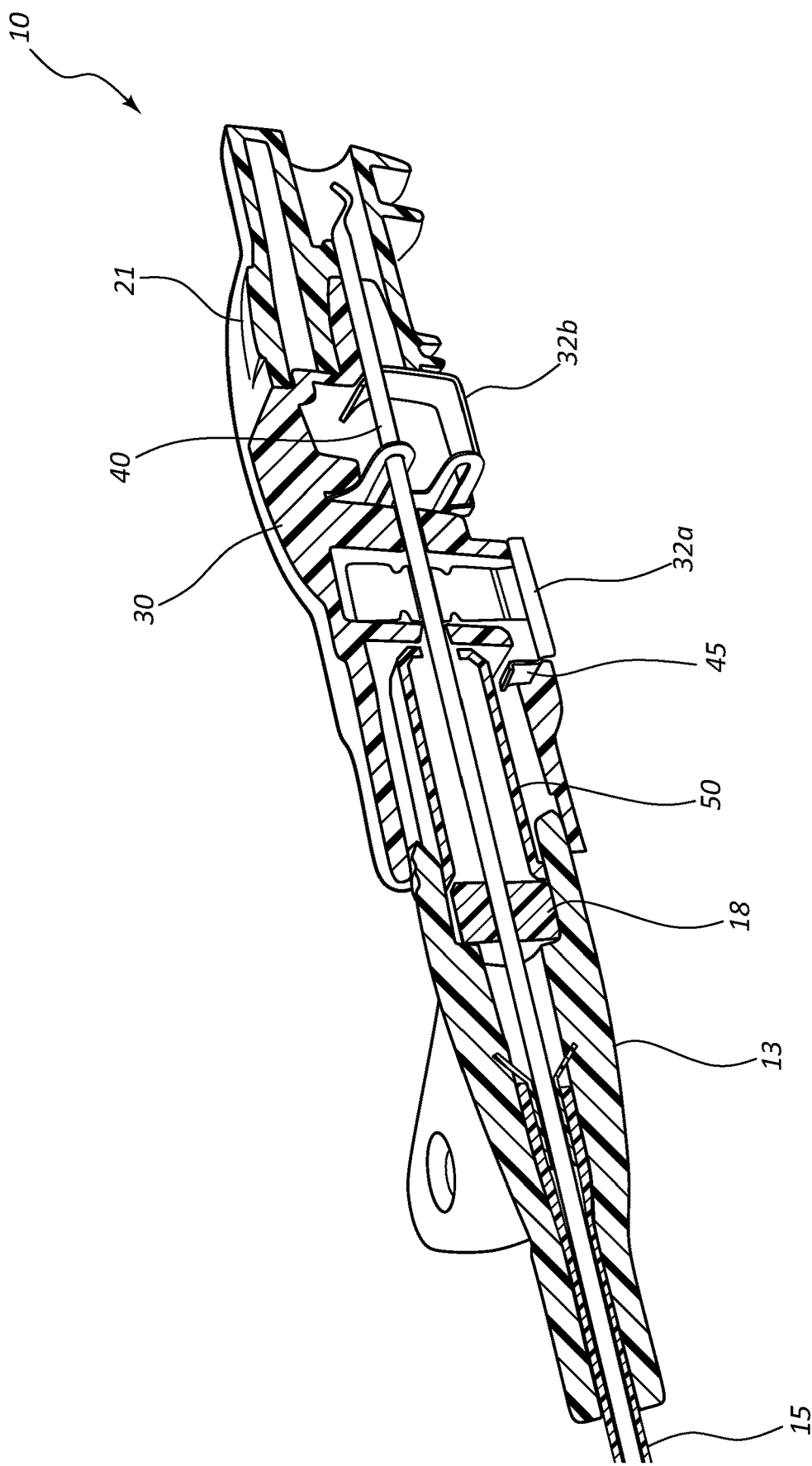
FIG. 9, shown in parts A and B, provides a cross-section view of an extravascular access device in accordance with a representative embodiment of the present invention.
Figure 9B:
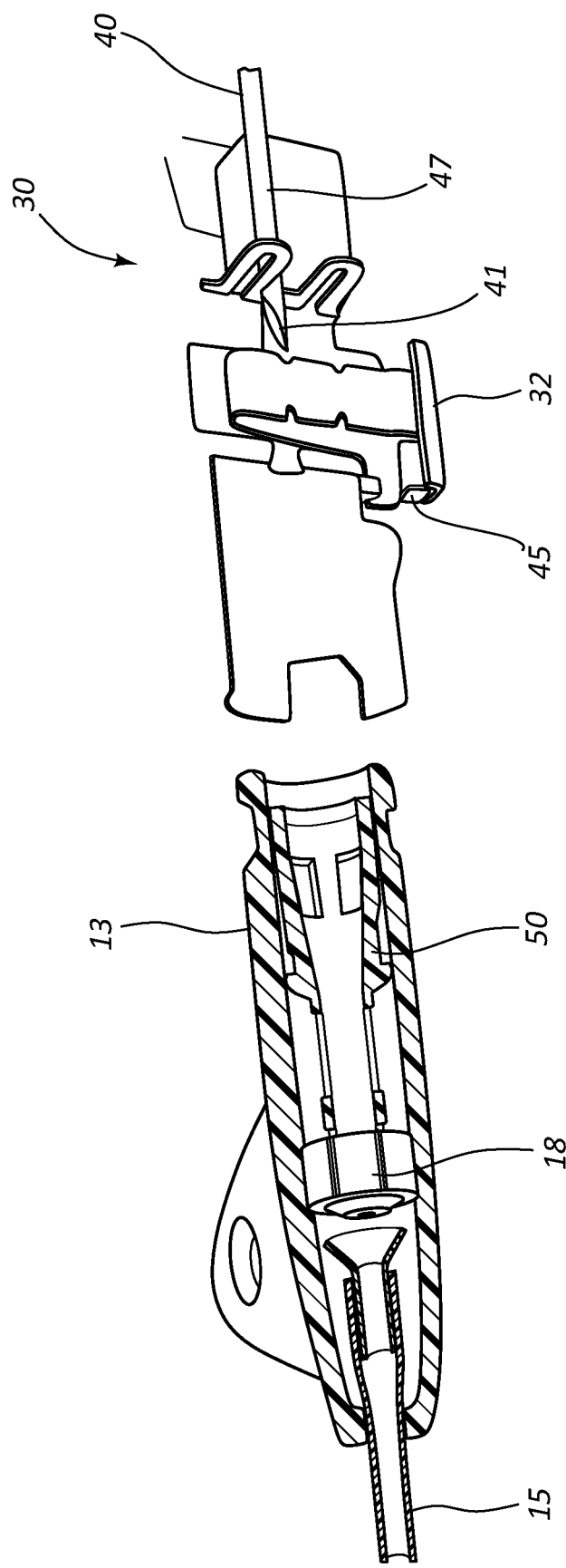
Figure 10A:
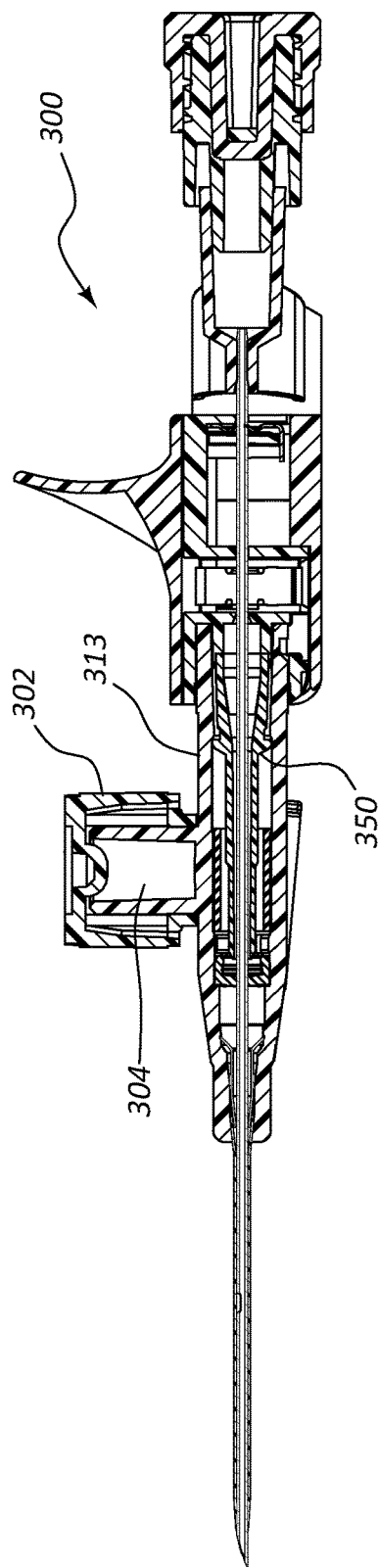
FIG. 10, shown in parts A-D, provides various plan and cross-section views of an extravascular access device in accordance with a representative embodiment of the present invention.
Figure 10B:
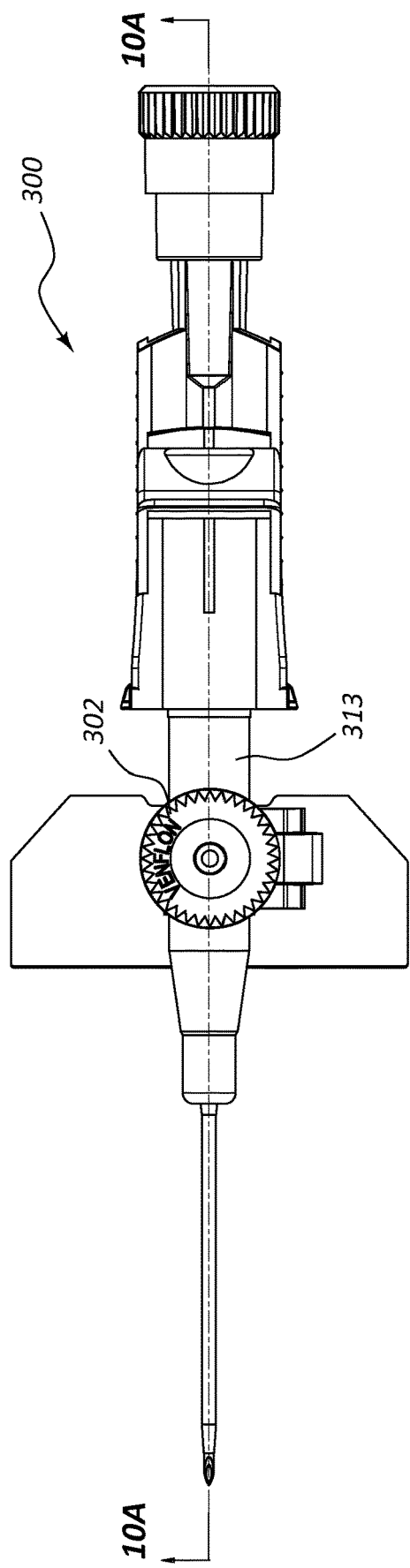
Figure 11A:
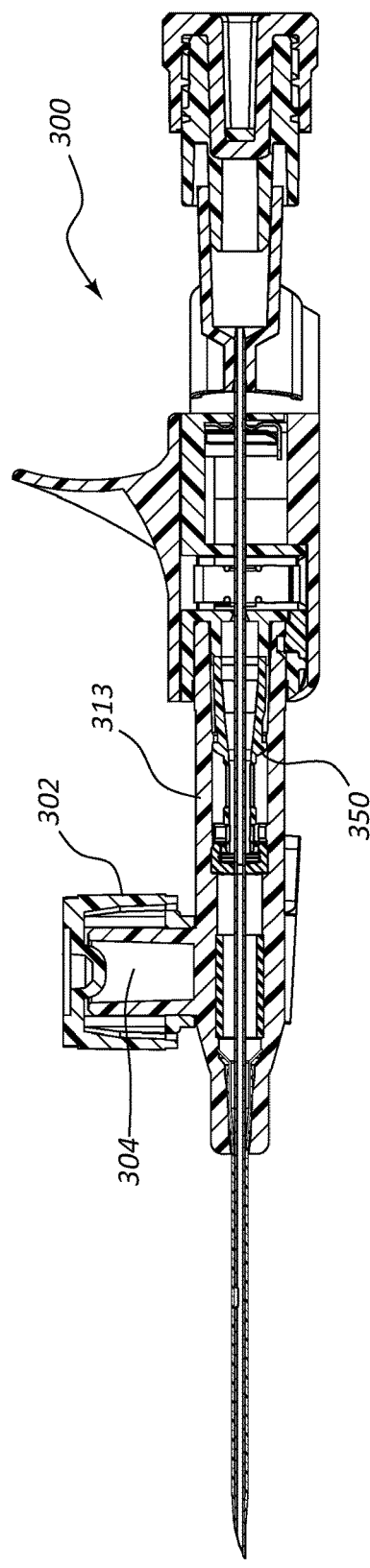
FIG. 11, shown in parts A-D, provides various plan and cross-section views of an extravascular access device in accordance with a representative embodiment of the present invention.
Figure 11B:
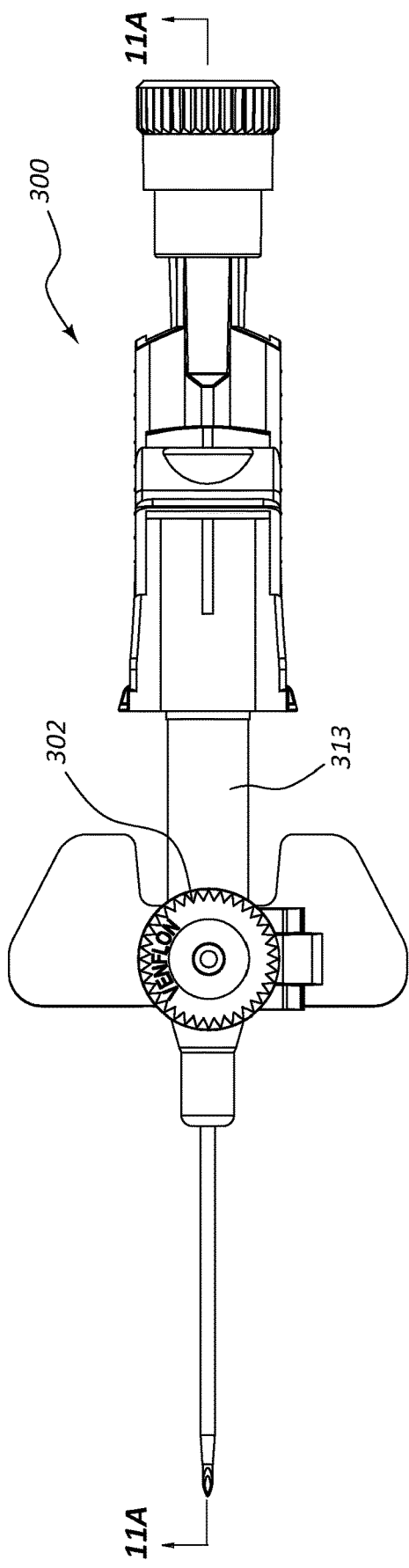
Figure 12A:
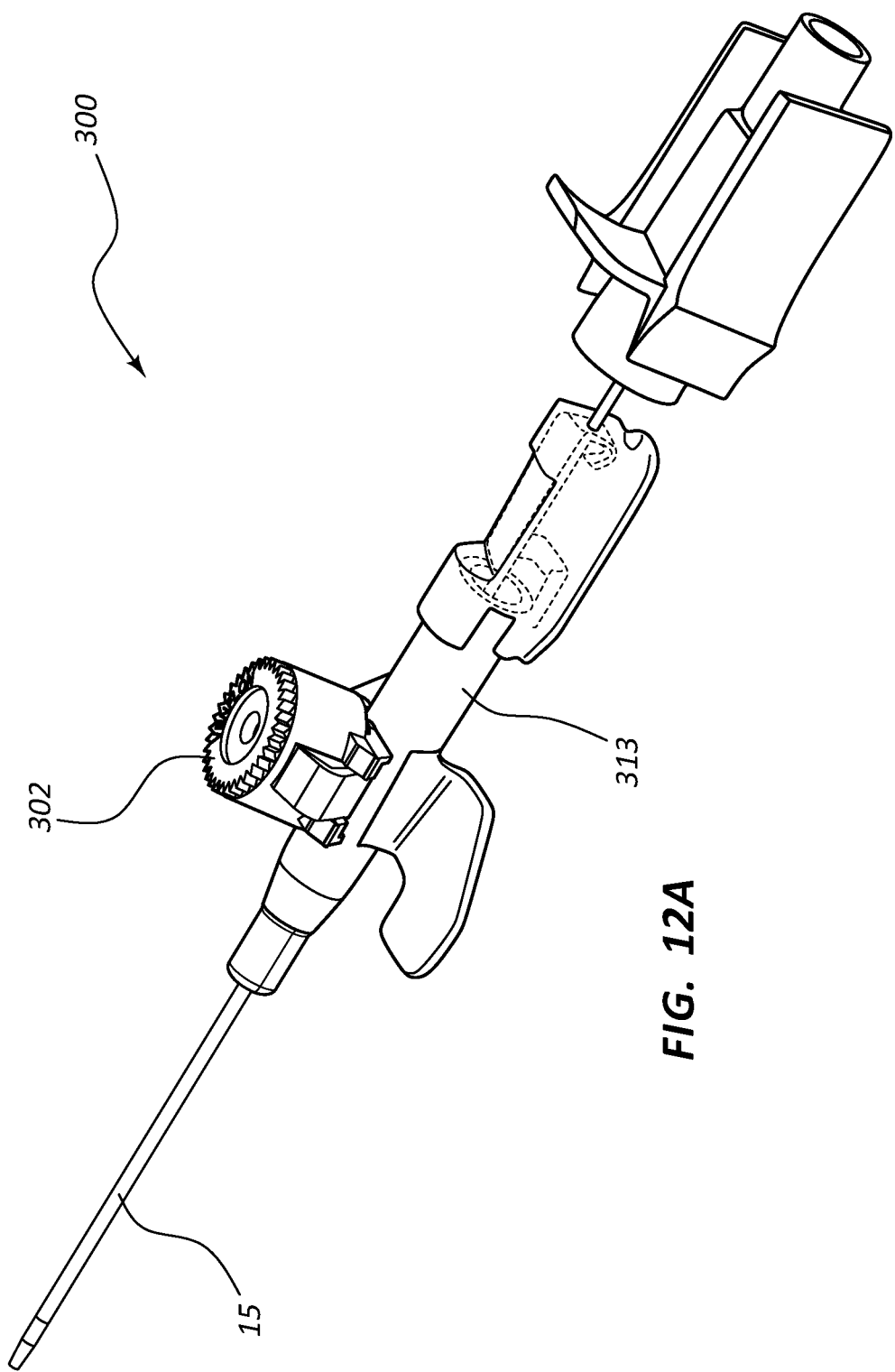
FIGS. 12A-17B provide various views of acceptable combinations of the features disclosed herein to provide an extravascular access device in accordance with a representative embodiment of the present invention.
Figure 12B:
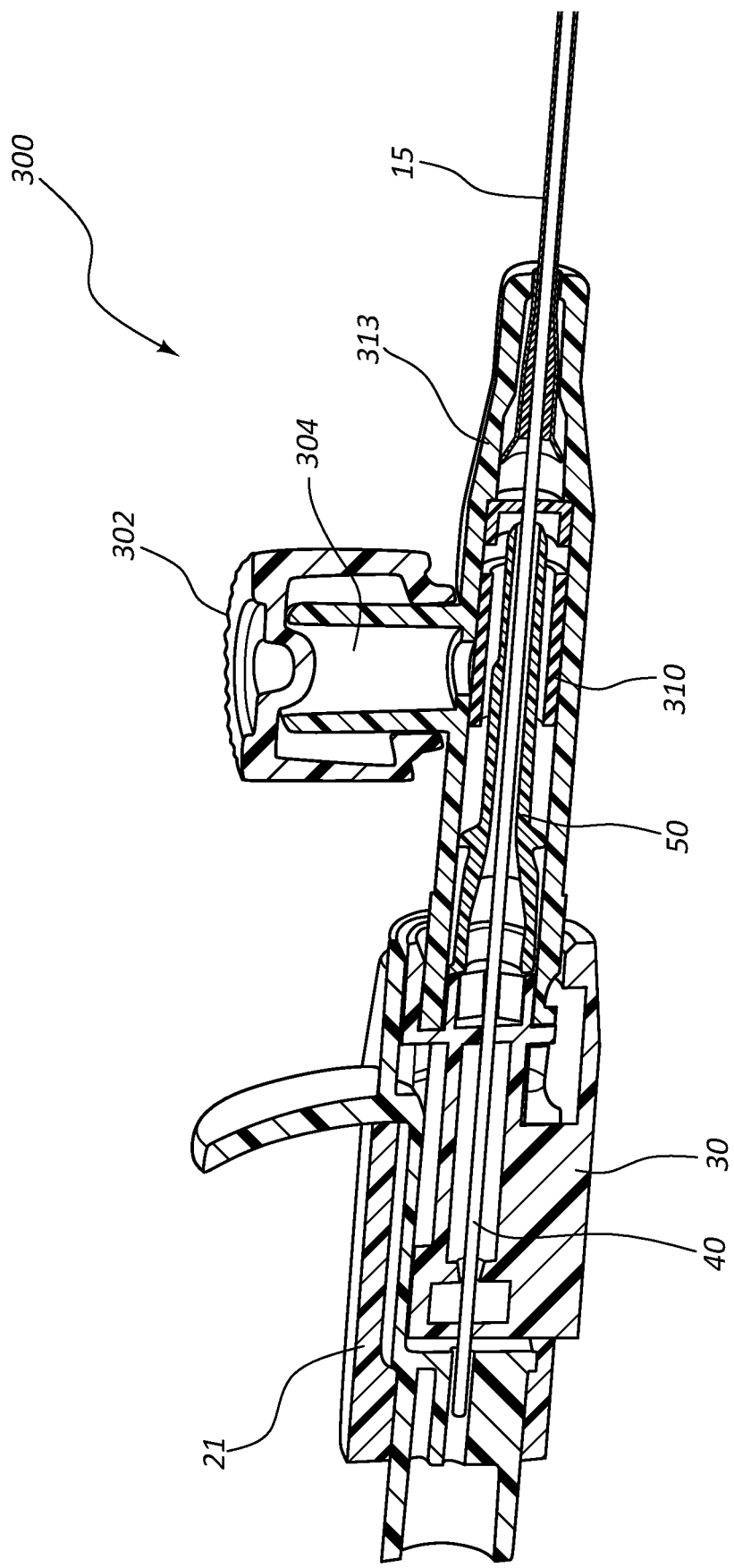
Figure 13:
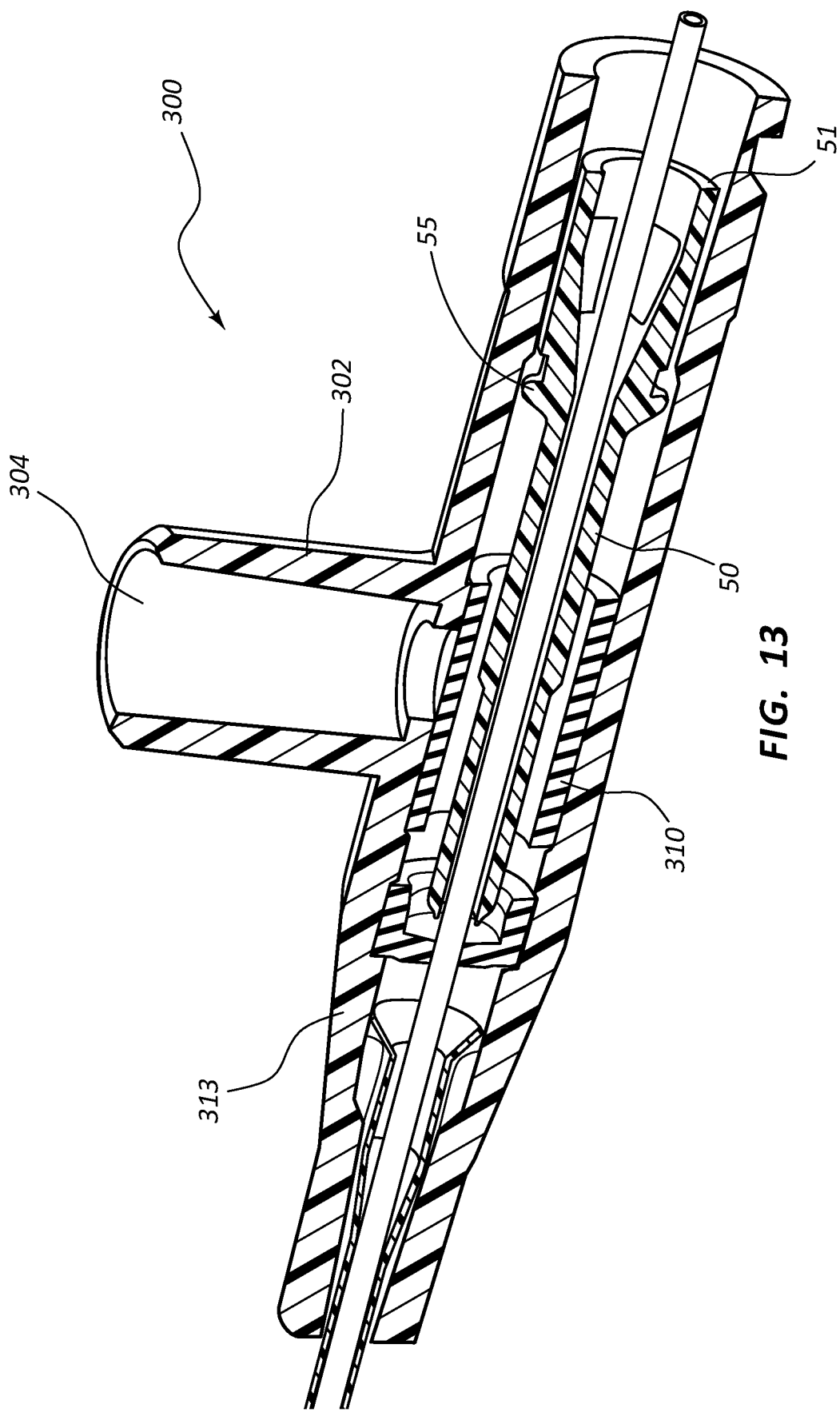

In some instances, clip 32 may be divided into two or more pieces. For example, a first piece may be configured to providing an interlocking action to release catheter adapter 13, and a second piece may be configured to trap a ferrule or crimp on needle 40, thereby preventing proximal of distal movement of needle 40. Referring now to FIGS. 9A and 9B, needle shield 30 may further include a first clip 32*a* and a second clip 32*b*, wherein first and second clips 32*a* and 32*b* are configured to retain distal tip 41 of needle 40 within needle shield 30. In some instances, first clip 32*a* is further configured to temporarily interconnect needle shield 30 and catheter adapter 13, as discussed previously.

In some instances, clip 32 is used with a second member as a housing. Clip 32 may also be used as only a safety mechanism, while the second member provides an interlocking feature. For example, in some embodiments a second member comprises a plurality of fingers that are configured to overlap the Luer connector of catheter adapter 13 to interlock catheter adapter 13 and needle shield 30 via a friction interface.

Any of the embodiments of the present invention may further comprise an access port 302, as shown in FIGS. 10A-17B. Port 302 generally comprises a portion of catheter adapter 313. In some instances, access port 302 comprises a cylinder coupled to the outer surface of catheter adapter 313, the cylinder having an inner lumen 304 that is in fluid communication with an inner lumen or fluid pathway of catheter adapter 313. Access port 302 further comprises an inner diameter that is configured to receive an external device, such as a needleless connector. In some instances, access port 302 comprises a removable cap or lid 306 that protects port 302 from contamination. In some instances, lid 306 is hingedly coupled to the base of access port 302.

In some embodiments, system 300 further comprises a defeatable barrier 310 that is seated into an annular groove formed on the inner surface of catheter adapter 313 and interposed between inner lumen 304 and the fluid pathway of catheter adapter 313. In some instances, barrier 310 comprises a tubular valve having an outer surface that forms an interface with inner lumen 304. Barrier 310 is defeated when an external device is inserted into inner lumen 304 and contacts the outer, exposed surface of barrier 310. When contacted by the external device, the tubular structure of barrier 310 slightly collapses thereby breaking the interface between the outer surface of barrier 310 and inner lumen 304. A fluid may then be added to the fluid pathway or lumen of catheter adapter 313. Alternatively, in some instances fluid pressure from the external device builds up within access port 302 until the interface between the outer surface of barrier 310 and inner lumen 304 is defeated. The fluid within access port 302 is then added to the fluid pathway or lumen of catheter adapter 313 via the temporarily defeated barrier 310. Upon removal of the external device, the resilient defeatable barrier 310 resumes its original shape thereby reestablishing the sealed interface with inner lumen 304.

Referring now to FIGS. 10A-10D, an assembly extravascular system 300 is shown in various plan and cross-section views, prior to catheterization. In some embodiments, system 300 comprises a blood control septum 18 that is placed within catheter adapter 313 at a position that is downstream or distal from access port 302. Thus, system 300 further comprises an elongated septum activator 350. Elongated septum activator 350 comprises an extended distal end 353 that is configured to pass through defeatable barrier 310 and reside in proximity to septum 18. This type of stacked or parallel configuration allows the overall length of catheter adapter 313 to be shortened.

In other embodiments, system 300 comprises a blood control septum 18 that is placed within catheter adapter 313 at a position that is upstream from access port 302, as shown in FIGS. 11A-11D. In these embodiments, system 300 includes a normal length septum activator 50. Unlike the shortened length of the catheter adapter 313, the linear or serial configuration of these embodiments may require that the overall length of catheter adapter 313 be extended.

System 300 may include any combination of external needle shield, internal blood control septum, and septum activator as disclosed herein. Examples of various acceptable combinations are shown in FIGS. 12A-17B. As previously mentioned, any of the embodiments described in FIGS. 1-9B may be modified to include any of the features of the embodiments shown in FIGS. 10A-17B, and in particular these embodiments may be modified to include an access port 302 and defeatable barrier 310.

Figure 14A:
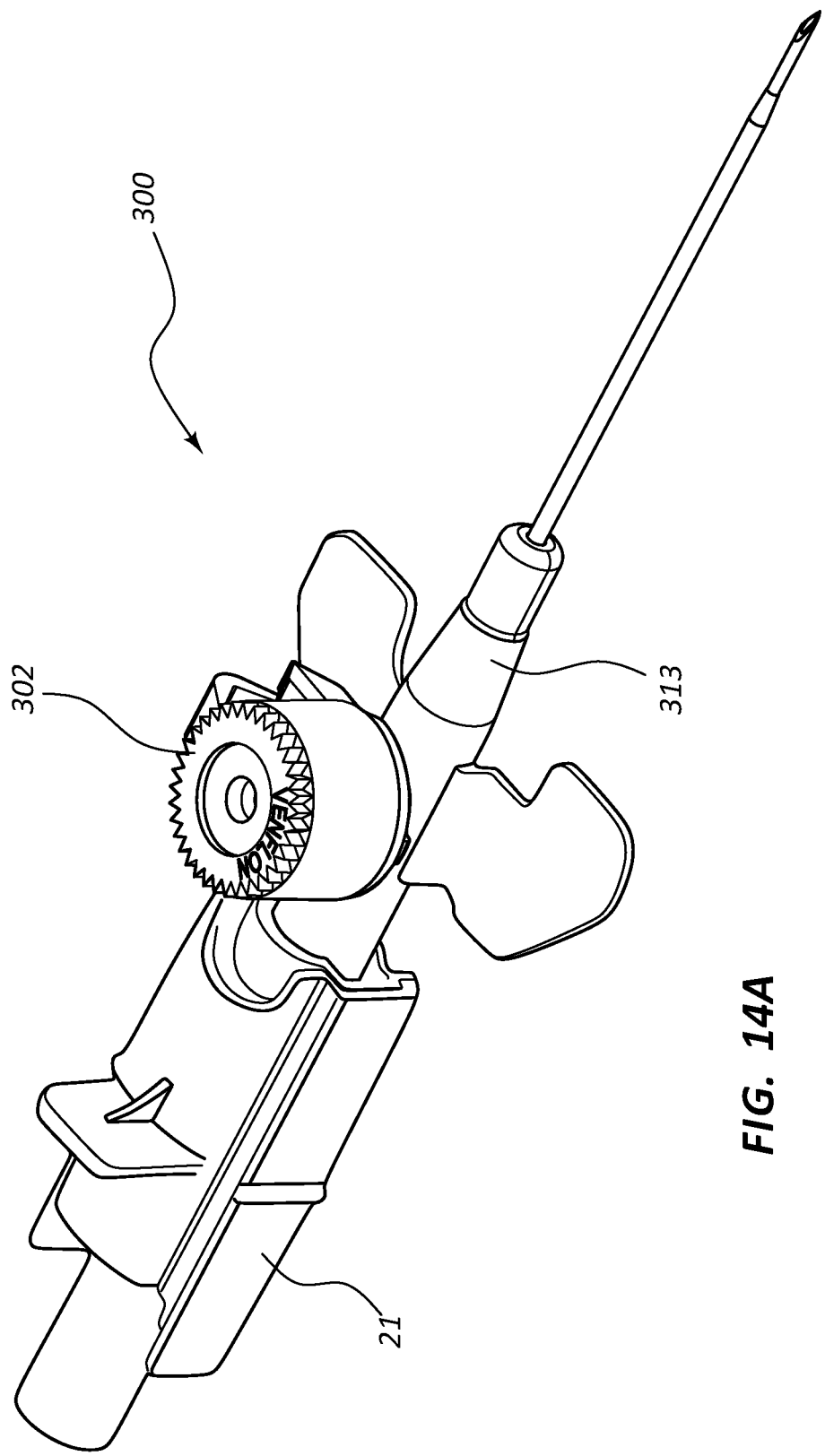
Figure 14B:
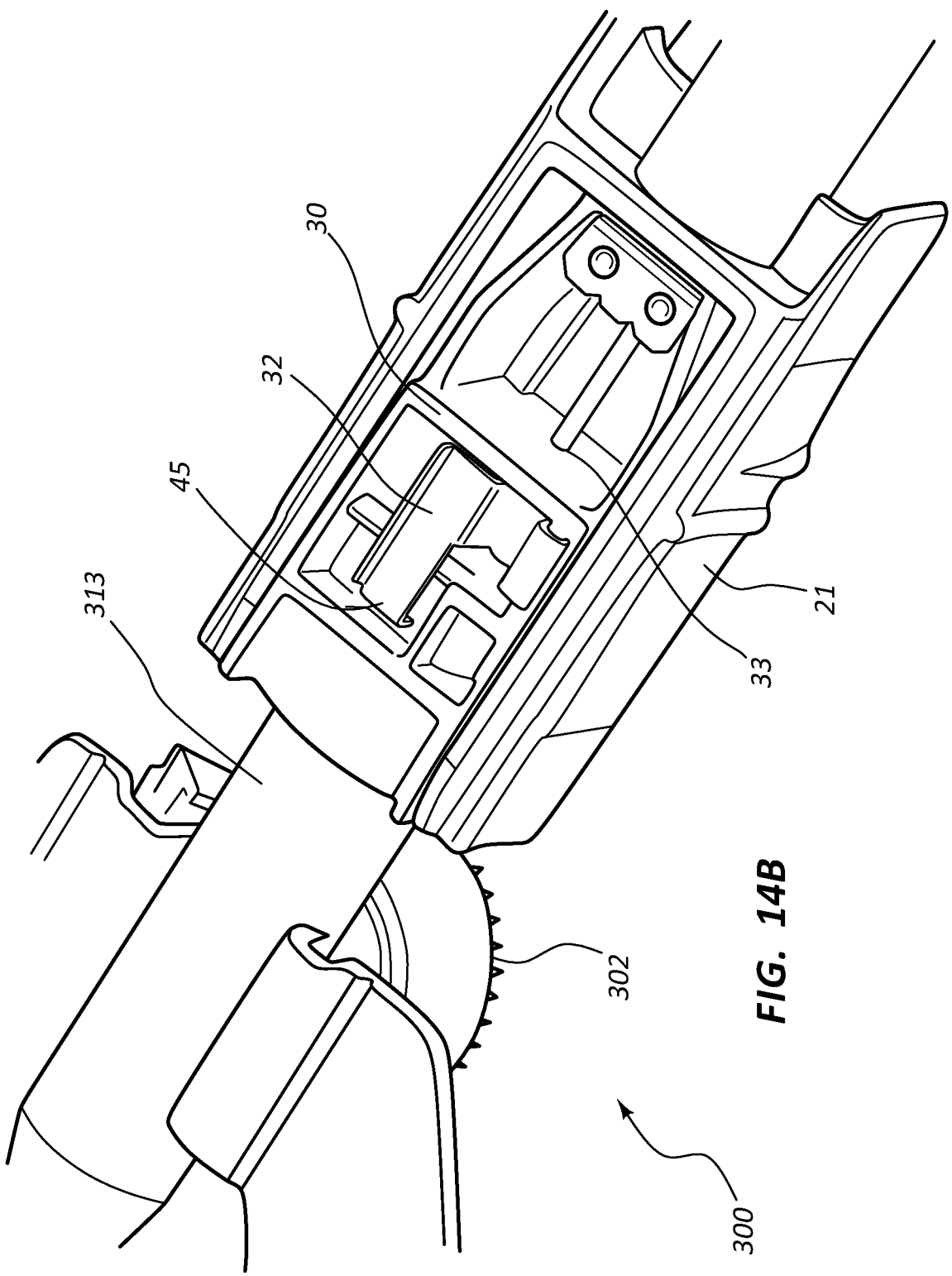
Figure 14C:
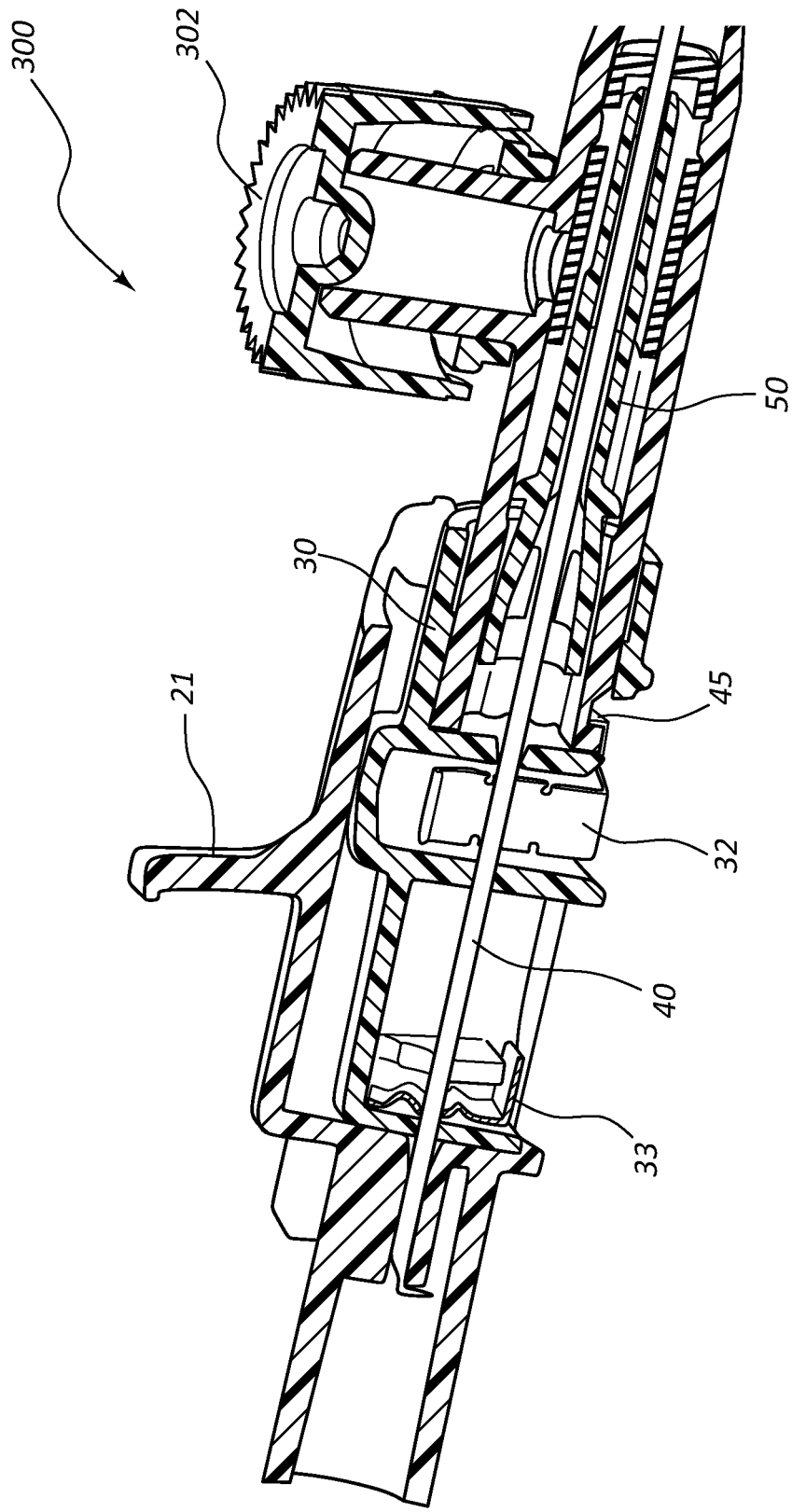
Figure 15A:
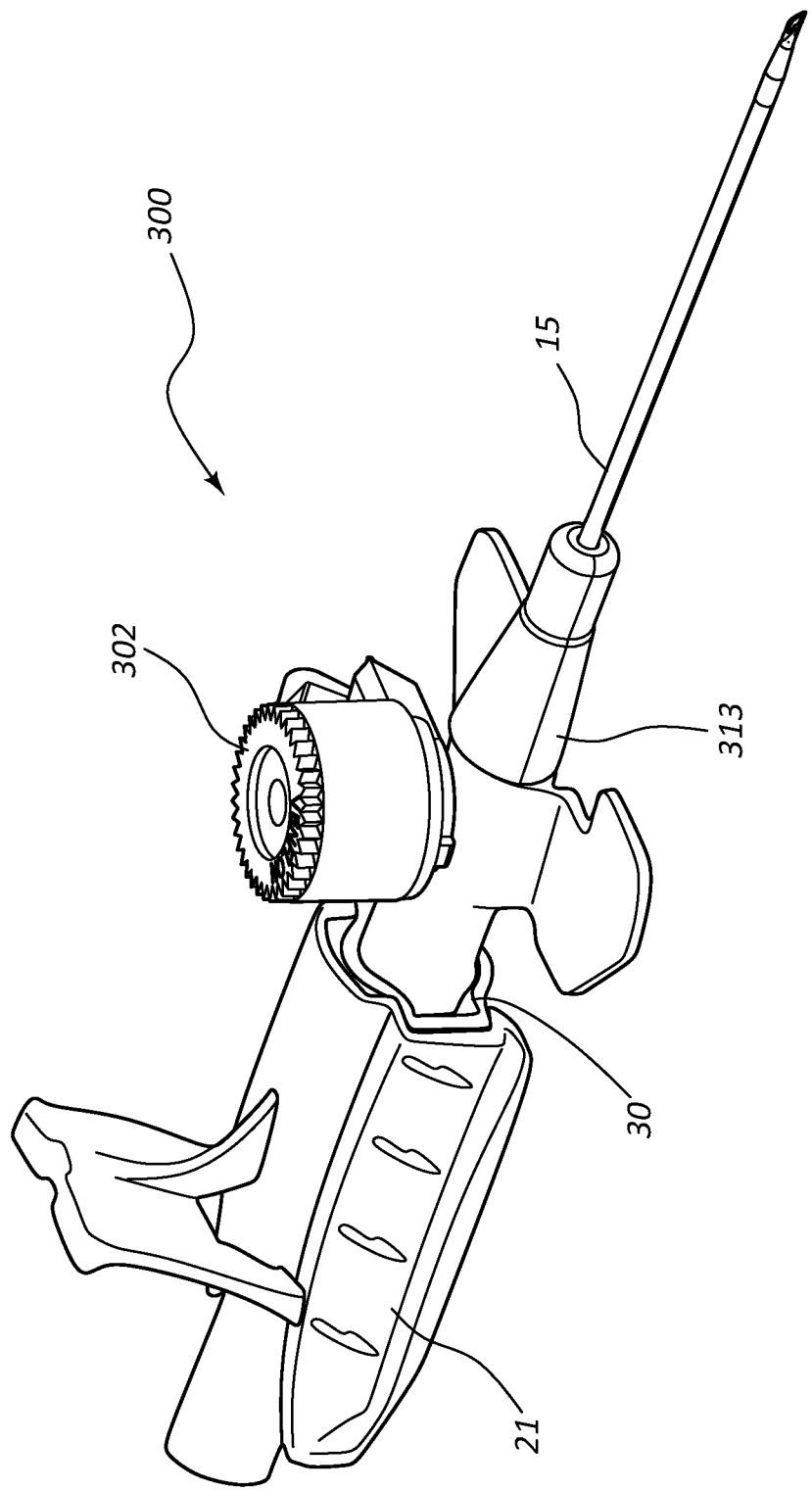
Figure 15B:
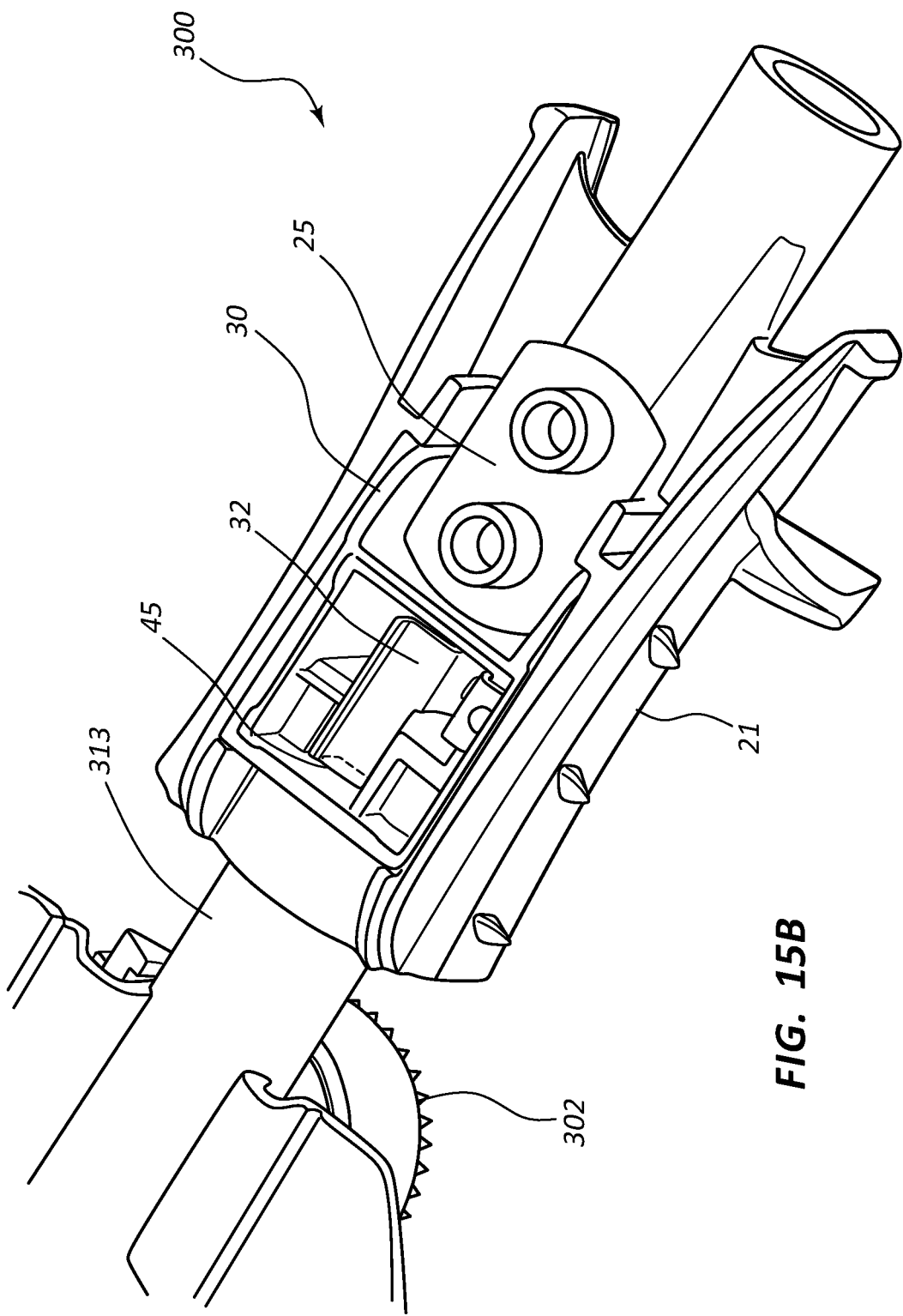
Figure 15C:
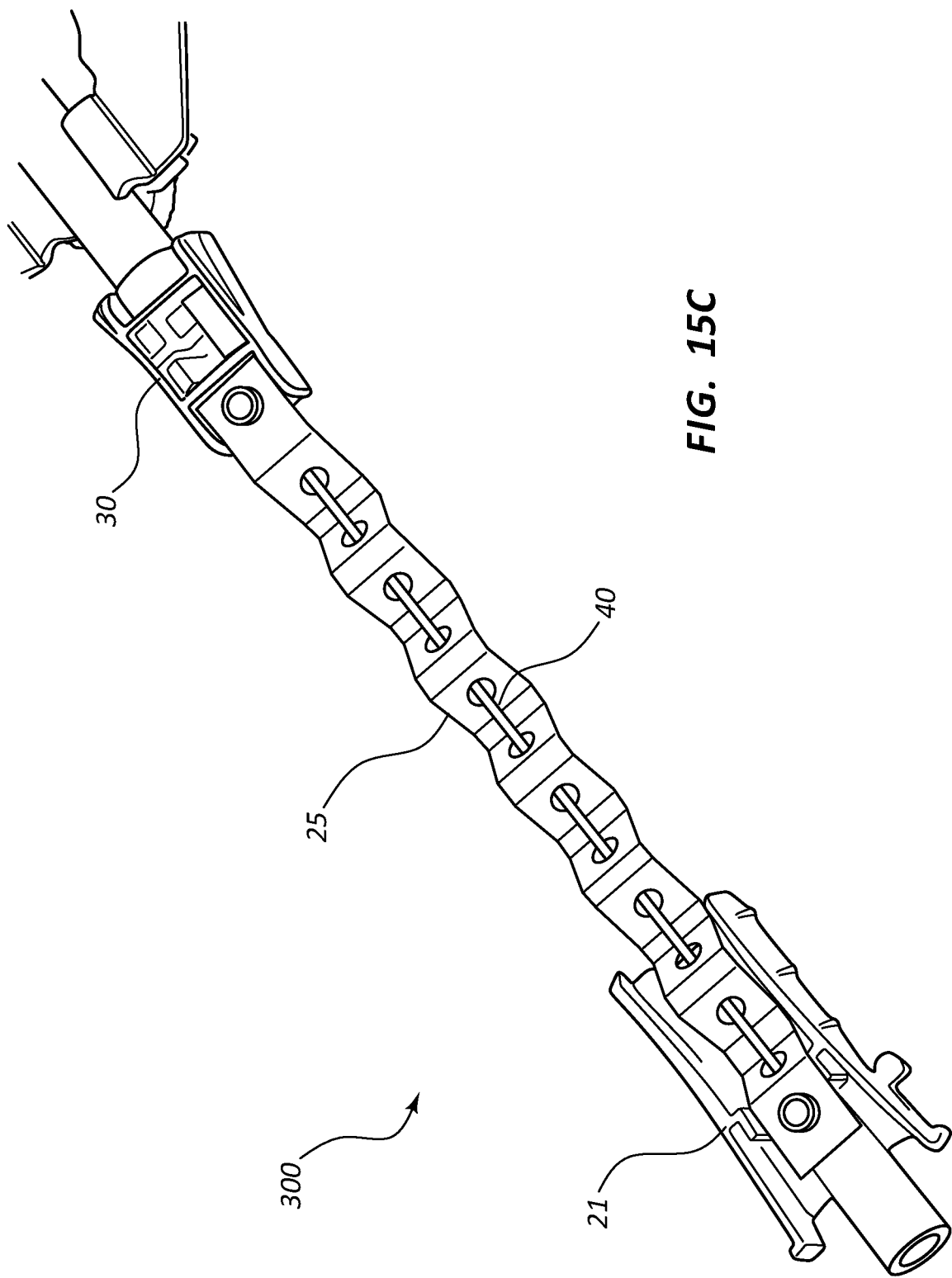
Figure 16:
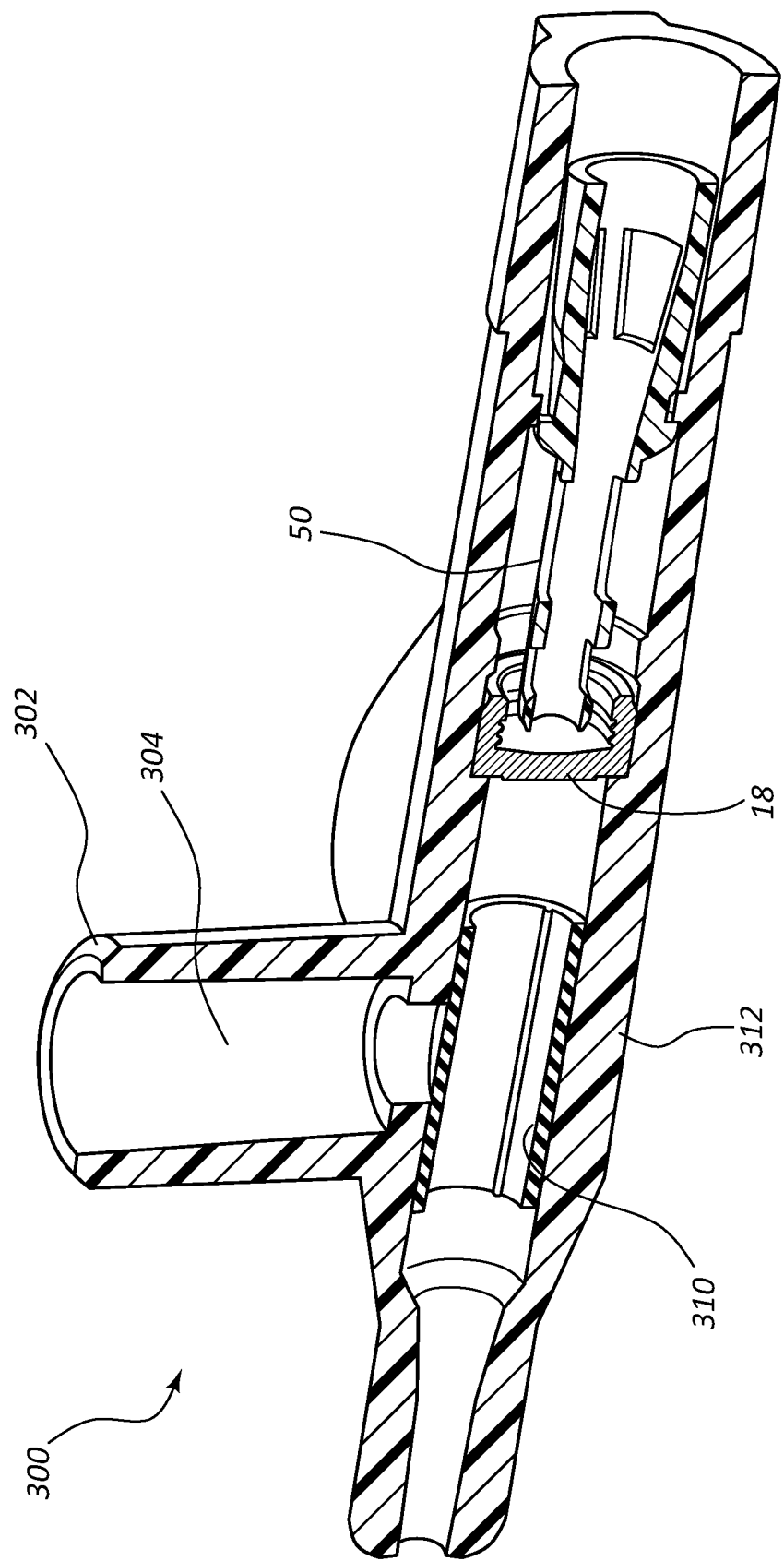
Figure 17A:
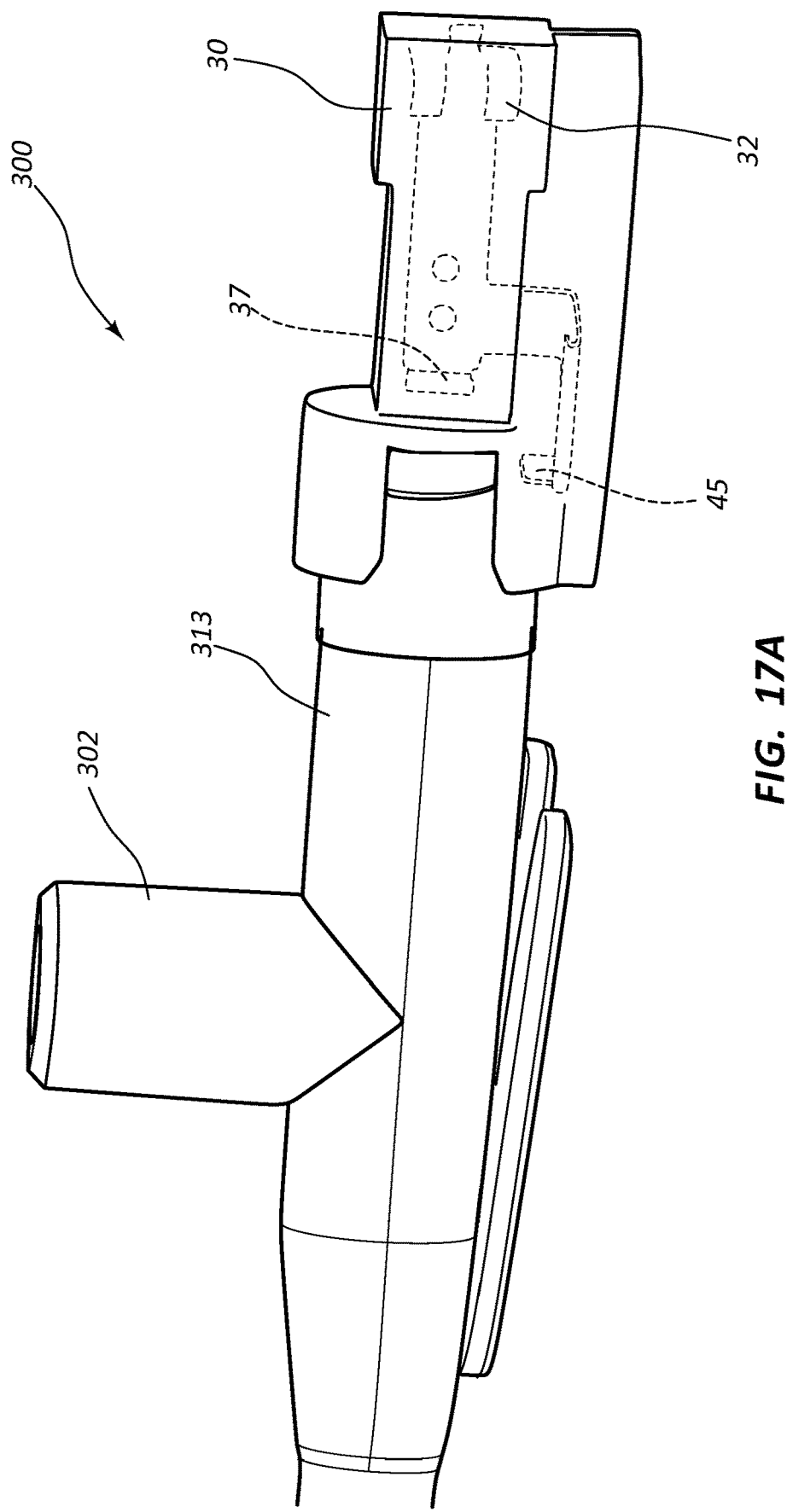
Figure 17B:
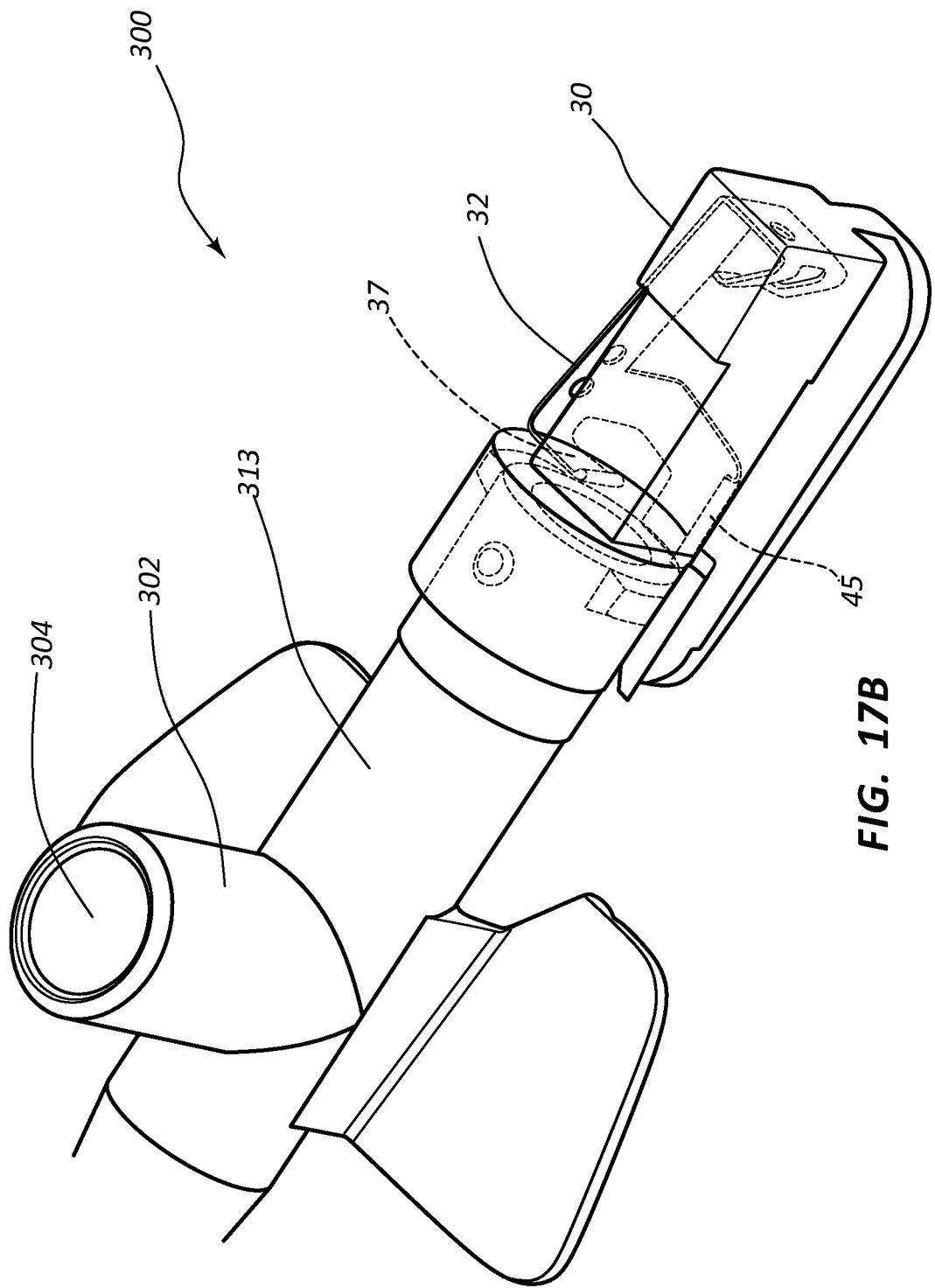

In some instances, system 300 may include a crimp or ferrule retention washer 33, as shown in FIGS. 14B and 14C. Access port 302 may further include one or more bumps or outward protrusions configured to retain cap 306 on the outer surface of port 302.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

What is claimed is:

1. An extravascular system for accessing the vasculature of a patient, comprising:
    a catheter adapter having a distal end, a proximal opening and a lumen disposed therebetween, the distal end supporting a catheter;
    an access port coupled to an outer surface of the catheter adapter and having an inner lumen that is in fluid communication with the lumen of the catheter adapter;
    a blood control valve disposed within the lumen of the catheter adapter and dividing the lumen of the catheter adapter into a proximal fluid chamber and a distal fluid chamber;
    a plurality of grooves forming air channels disposed on an outer surface of the valve and/or on an inner surface of the lumen of the catheter adapter;
    a defeatable barrier disposed within the lumen of the catheter adapter and selectively forming a sealed interface with the inner lumen of the access port;
    an activator having a base and a probe end, the activator being movably positioned within the proximal fluid chamber; and
    a housing comprising a distal end and a proximal end; wherein
    an outer surface of the catheter adapter is disposed within the distal end of the housing; and
    the distal end of the housing extends distal to the base of the activator when the activator is in initial position.

2. The system of claim 1, wherein: the housing is removably coupled to the proximal opening of the catheter adapter; and further comprising a safety clip configured to secure a distal tip of an introducer needle.

3. The system of claim 2, wherein the safety clip is configured to engage and disengage the catheter adapter.

4. The system of claim 3, further comprising a pawl that forms a portion of the safety clip and selectively positioned within a proximal rim of the catheter adapter to maintain engagement between the housing and the catheter adapter.

5. The system of claim 4, wherein upon removal of the introducer needle from the catheter adapter, the safety clip is released and the pawl is disengaged from the proximal rim of the catheter adapter, thereby disconnecting the housing from the catheter adapter.

6. The system of claim 2, further comprising:
a flag that extends from a body of the safety clip; wherein the flag is biased away from a distal aperture disposed in a first wall of the housing into a biased position when the introducer needle extends through the distal aperture; and
in response to the distal tip of the introducer needle being withdrawn into the housing and disposed proximal to the distal aperture, the flag is released from the biased position and blocks the distal aperture thereby preventing the distal tip from exiting the distal end of the housing through the distal aperture.

7. The system of claim 2, wherein the safety clip avoids contact with the catheter adapter.

8. The system of claim 1, further comprising a tether having a first end coupled to a needle hub of an introducer needle and a second end coupled to the housing.

9. The system of claim 8, wherein the housing comprises a needle shield.

10. The system of claim 8, wherein the tether has a length that is less than a distance between distal tip and a base of the introducer needle.

11. The system of claim 8, wherein the tether prevents removal of distal tip of the needle from the housing.

12. The system of claim 1, wherein the blood control valve is distal to the defeatable barrier in the lumen of the catheter adapter.

13. The system of claim 1, wherein the defeatable barrier is distal to the blood control valve in the lumen of the catheter adapter.

14. The system of claim 1, wherein the defeatable barrier is independent and separate from the blood control valve.

15. The system of claim 1, further comprising:
a washer disposed within a proximal end of the housing and separated from a safety clip by a wall; wherein
the washer comprises an aperture configured to prevent passage of a needle feature of an introducer needle, the washer and the needle feature thereby securing a distal tip of the introducer needle in the housing when the distal tip of the introducer needle is withdrawn into the housing.

16. The system of claim 1, wherein the blood control valve comprises a septum valve.

* * * * *